(12) United States Patent
Kreitenberg et al.

(10) Patent No.: US 11,413,361 B2
(45) Date of Patent: *Aug. 16, 2022

(54) MOBILE UV DISINFECTING SYSTEM

(71) Applicant: DIMER, LLC, Los Angeles, CA (US)

(72) Inventors: Arthur Kreitenberg, Los Angeles, CA (US); Elliot M. Kreitenberg, Los Angeles, CA (US)

(73) Assignee: DIMER, LLC, Los Angeles, CA (US)

( * ) Notice: Subject to any disclaimer, the term of this patent is extended or adjusted under 35 U.S.C. 154(b) by 254 days.

This patent is subject to a terminal disclaimer.

(21) Appl. No.: 16/782,691

(22) Filed: Feb. 5, 2020

(65) Prior Publication Data
US 2020/0268915 A1    Aug. 27, 2020

Related U.S. Application Data

(60) Provisional application No. 62/809,969, filed on Feb. 25, 2019.

(51) Int. Cl.
*A61L 2/00*    (2006.01)
*A61L 2/10*    (2006.01)

(52) U.S. Cl.
CPC ............. *A61L 2/0047* (2013.01); *A61L 2/10* (2013.01); *A61L 2202/16* (2013.01); *A61L 2202/21* (2013.01)

(58) Field of Classification Search
CPC .... A61L 2/10; A61L 2202/16; A61L 2202/21; A61L 2/0047
See application file for complete search history.

(56) References Cited

U.S. PATENT DOCUMENTS

| 2,273,449 A | 2/1942 | Plishker |
| 5,338,169 A | 8/1994 | Buckley |
| (Continued) | | |

FOREIGN PATENT DOCUMENTS

| CN | 2621044 Y | 6/2004 |
| CN | 101756678 | 6/2010 |
| (Continued) | | |

OTHER PUBLICATIONS

International Search Report and Written Opinion, dated Jun. 4, 2020, from corresponding International Patent App. No. PCT/US2020/016792.

(Continued)

*Primary Examiner* — Sean E Conley
(74) *Attorney, Agent, or Firm* — Greenberg Traurig, LLP

(57) ABSTRACT

Sanitizing surfaces comprising a sanitization device including a mobile body; and extending the sanitization device (102) laterally from the mobile body across a surface. A source of UV radiation (104) is mounted on the sanitization device. The sanitization device moves across the surface; exposing the surface to UV radiation produced by the source; directing a source of UV radiation to the surface at a predetermined dosage while the device moves over surface. Moving and locating the sanitization device can be inwardly and outwardly relative to the mobile body to extend at different angles being from a horizontal angle relative to the mobile body to a non-horizontal angle relative to the mobile body and to effect sanitization when so extended. The device is operable upwardly and downwardly across the surface while effecting the sanitation.

19 Claims, 19 Drawing Sheets

(56) References Cited

U.S. PATENT DOCUMENTS

| | | |
|---|---|---|
| 5,369,892 A | 12/1994 | Dhaemers |
| 5,673,918 A | 10/1997 | Bigari |
| 5,920,075 A | 7/1999 | Whitehead |
| 5,959,423 A | 9/1999 | Nakanishi et al. |
| 6,311,974 B1 | 11/2001 | Koga |
| 6,370,453 B2 | 4/2002 | Sommer |
| 6,389,639 B1 | 5/2002 | Worsham |
| 6,419,190 B1 | 7/2002 | Nguegang |
| 6,565,668 B1 | 5/2003 | Sandberg et al. |
| 6,779,714 B2 | 5/2004 | Webb |
| 6,787,782 B1 | 9/2004 | Krosney et al. |
| 6,889,449 B2 | 5/2005 | Silver |
| 6,992,301 B2 | 1/2006 | Fenc |
| 7,204,208 B2 | 4/2007 | Johnson et al. |
| 7,459,694 B2 | 12/2008 | Scheir et al. |
| 7,459,695 B2 | 12/2008 | Hanley et al. |
| 7,462,849 B2 | 12/2008 | Ferres et al. |
| 7,523,692 B1 | 4/2009 | Burns |
| 8,029,739 B2 | 10/2011 | Field et al. |
| 8,105,532 B2 | 1/2012 | Harmon et al. |
| 8,193,515 B2 | 6/2012 | Kreitenberg |
| 8,226,887 B2 | 7/2012 | Harmon et al. |
| 8,330,121 B2 | 12/2012 | Douglas |
| 8,907,304 B2 | 12/2014 | Kreitenberg |
| 8,999,238 B2 | 4/2015 | Kreitenberg |
| 9,095,633 B1 | 8/2015 | Dayton |
| 9,144,618 B2 | 9/2015 | Kreitenberg |
| 9,149,549 B2 | 10/2015 | Kreitenberg |
| 10,195,298 B2 | 2/2019 | Kreitenberg |
| 10,500,296 B2 * | 12/2019 | Kreitenberg .............. A61L 2/26 |
| 2004/0056201 A1 | 3/2004 | Fink et al. |
| 2004/0244138 A1 | 12/2004 | Taylor et al. |
| 2005/0022844 A1 | 2/2005 | Field et al. |
| 2005/0159275 A1 | 7/2005 | Bullman et al. |
| 2006/0216193 A1 | 9/2006 | Johnson et al. |
| 2007/0158499 A1 | 7/2007 | Whittingham |
| 2008/0056933 A1 | 3/2008 | Moore et al. |
| 2008/0184518 A1 | 8/2008 | Taylor et al. |
| 2009/0193676 A1 | 8/2009 | Shnengguang et al. |
| 2010/0028201 A1 | 2/2010 | Neister |
| 2011/0082668 A1 | 4/2011 | Escrig et al. |
| 2011/0167574 A1 | 7/2011 | Stout et al. |
| 2012/0221192 A1 | 8/2012 | Seibt |
| 2012/0223216 A1 | 9/2012 | Flaherty et al. |
| 2013/0000675 A1 | 1/2013 | Hong et al. |
| 2013/0270459 A1 | 10/2013 | Fontani |
| 2014/0044590 A1 | 2/2014 | Trapani |
| 2014/0241941 A1 | 8/2014 | Kreitenberg |
| 2015/0209459 A1 | 7/2015 | Kreitenberg |
| 2017/0216473 A1 | 8/2017 | Rizzone |
| 2017/0326262 A1 | 11/2017 | Paver, Jr. |
| 2018/0256764 A1 | 9/2018 | Kreitenberg |
| 2018/0274219 A1 | 9/2018 | Arnott et al. |
| 2018/0296713 A1 | 10/2018 | Stibich et al. |

FOREIGN PATENT DOCUMENTS

| | | |
|---|---|---|
| CN | 202314543 U | 7/2012 |
| CN | 202554525 U | 11/2012 |
| DE | 3937706 | 5/1991 |
| GB | 2391799 | 2/2004 |
| JP | S63-135646 U | 9/1988 |
| JP | H10-57614 | 3/1998 |
| JP | 2000-325059 | 11/2000 |
| JP | 2005-013723 | 1/2005 |
| JP | 2007-082747 | 4/2007 |
| JP | 2009-291349 | 12/2009 |
| JP | 2011-098156 | 5/2011 |
| WO | WO2008/010684 | 1/2008 |
| WO | WO2014/036217 | 3/2014 |
| WO | 2018089288 A1 | 5/2018 |

OTHER PUBLICATIONS

European Search and Written Opinion, dated Mar. 14, 2022, from related European Patent App. No. 20763235.

Universal Joint, Wikipedia [retrieved on Mar. 24, 2022] from the Internet at: https://en.wikipedia.org/wiki/Universal_joint.com.

* cited by examiner

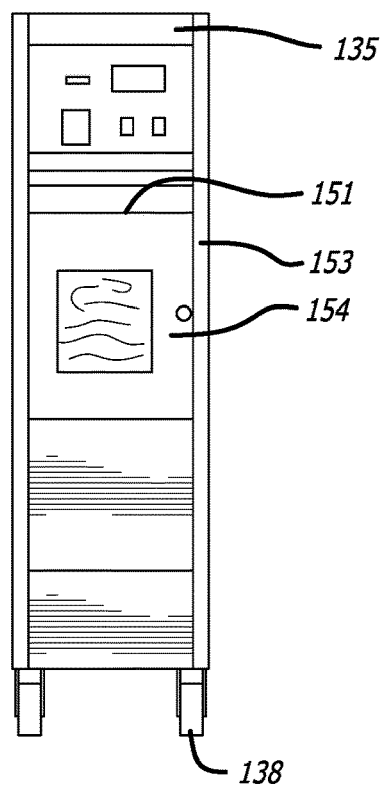
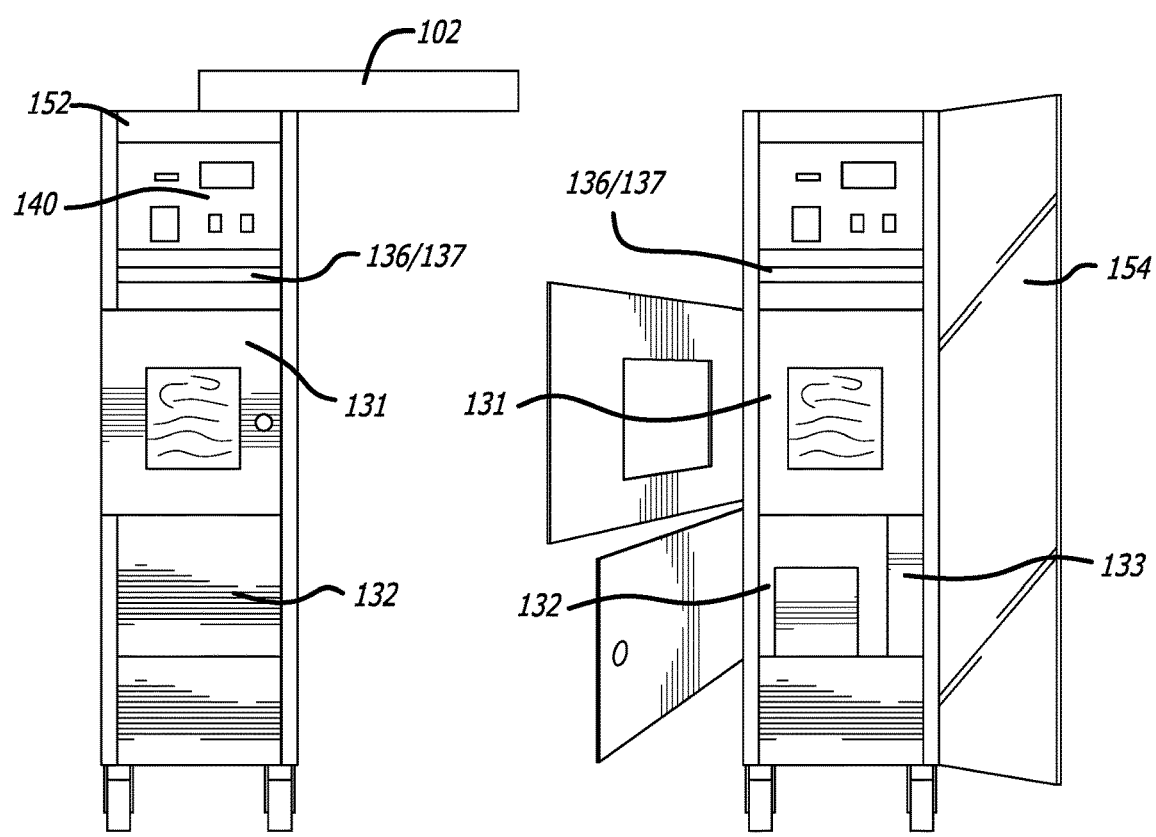
FIG. 6
FIG. 7
FIG. 8

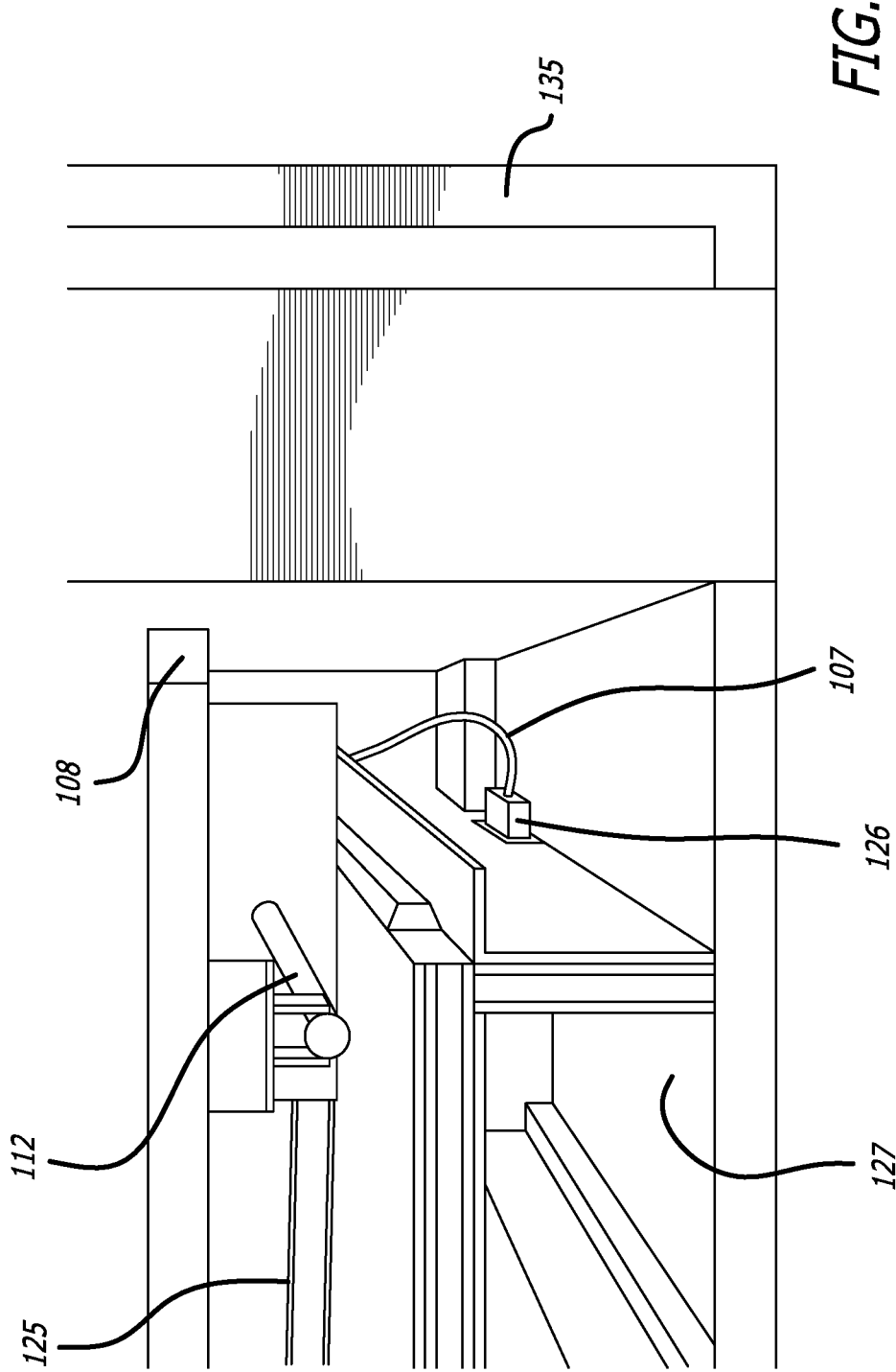

FIG. 24
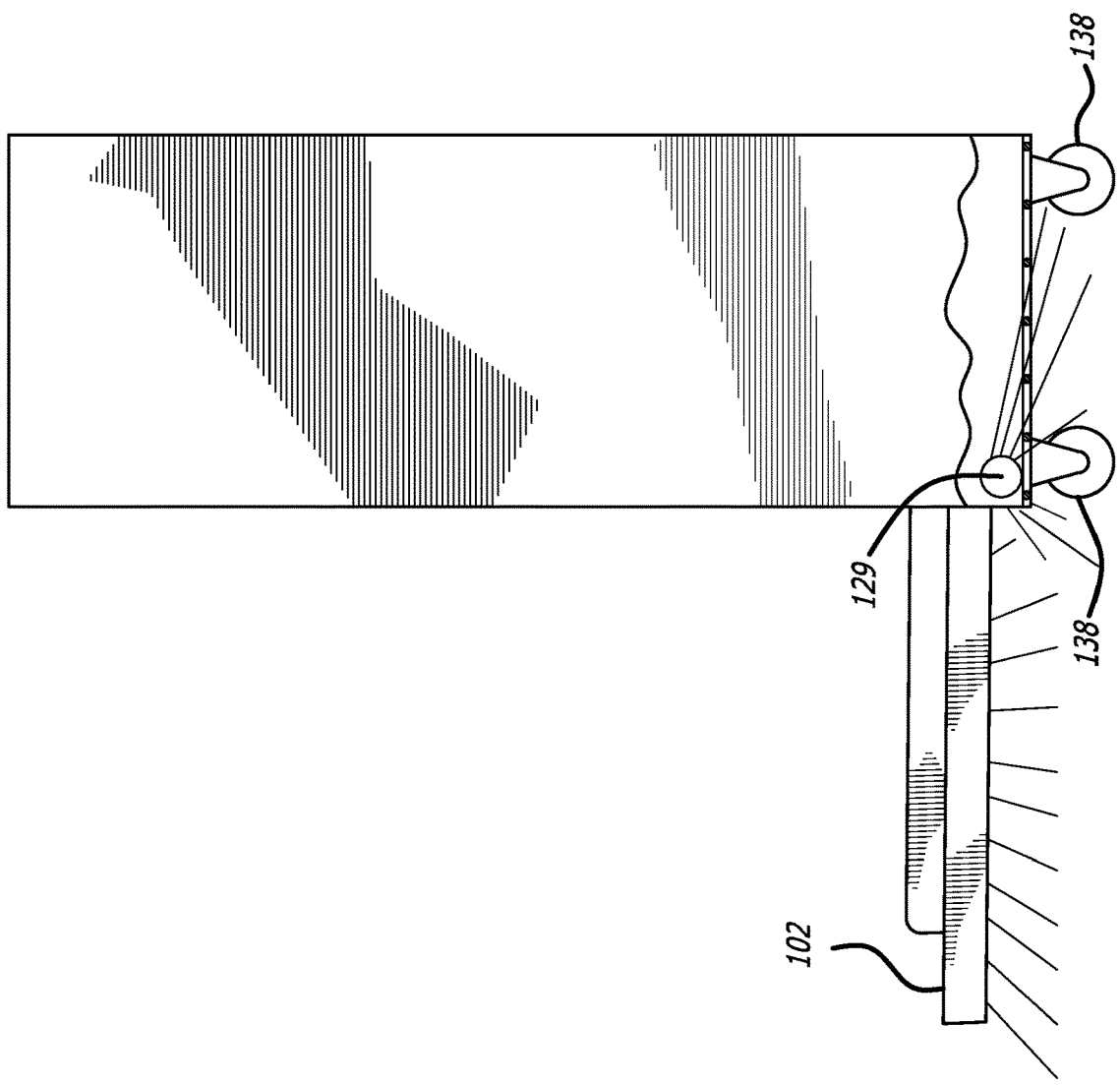
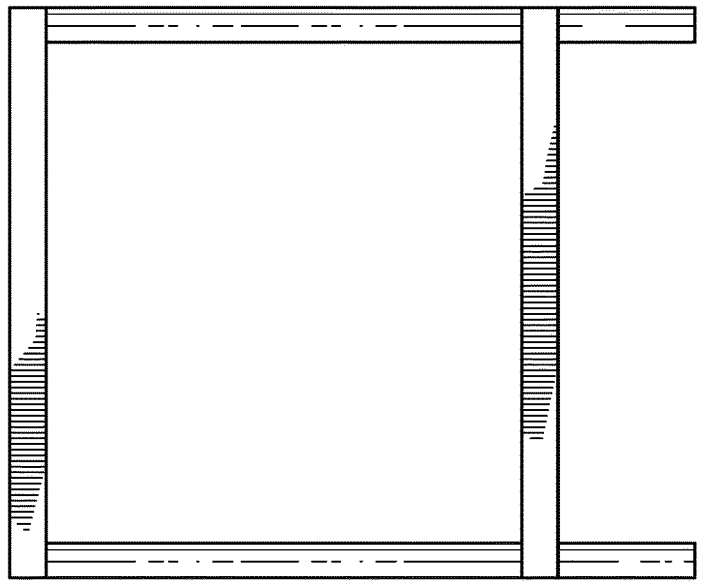

MOBILE UV DISINFECTING SYSTEM

RELATED APPLICATION

This application relates to U.S. Provisional App. No. 62/809,969 for MOBILE UV DISINFECTING SYSTEM filed Feb. 25, 2019. Priority is claimed from that application and the contents thereof are incorporated by reference herein in its entirety.

BACKGROUND

There is a great need for rapid disinfection of surfaces in many settings including but not limited to healthcare, schools, airports, theatres, food preparation, sporting venues and prisons.

Within the healthcare space, several devices that emit ultraviolet (UV) light in the germicidal wavelength spectrum exist and have been reported to lower healthcare associated infections (HAIs). These devices are stationary and require manually relocating to several locations within a room or simultaneously using multiple devices to reach commonly touched surfaces. Because UV exposure to operator's eyes and skin has potentially harmful effects, the operator must leave the room and make sure no one enters during the disinfection cycle.

Existing UV emitting devices utilize UV sources that are most commonly fluorescent lamps or a pulsed-Xenon UV generator oriented in a primarily vertical orientation.

The effectiveness of germicidal UV light is highly dependent on the distance from UV source to the target surface as defined by the inverse square law and the rapid dissipation of UV light in air. Additionally, vertically oriented UV sources are far more effective on vertical than on horizontal surfaces.

Consequently, the UV source should optimally be parallel to and very close to the target surface for best results.

Many surfaces requiring disinfection are textured rather than smooth. This affects UV effectiveness because a textured surface has a far greater surface area than a smooth surface. This makes UV delivery rate and dose even more critical. Further, a textured surface provides "hiding places" for pathogens in the troughs, pits and valleys of the textured surface. For this reason, horizontal textured surfaces cannot be adequately disinfected with a vertically oriented UV source from the side in any time frame.

Prior art includes U.S. Pat. Nos. 8,907,304, 8,999,238, 9,149,549 and 10,195,298 issued to the current inventor, describing a mobile UV device for the disinfection of aircraft and other environments where people assemble, and germ transmission occurs.

SUMMARY

The current disclosure is a sanitization apparatus and method that utilizes a single segment wing that can selectively be fully deployed in multiple positions to provide UV sanitation to a surface while maintaining navigability and maintain operator safety.

BRIEF DESCRIPTION OF DRAWINGS

FIG. 6 is a drawing from the rear of the sanitation device in transportation mode.

FIG. 7 is a drawing from the rear of the sanitation device in a horizontal mode

FIG. 8 is a drawing from the rear of the sanitation device with compartment doors open

FIG. 10 is a drawing from above showing wing plugs and body receptacles.

FIG. 24 is a drawing of the sanitation device showing the device in the environment of a hospital and the wing in a horizontal position with radiation being extended downwardly from the wing on to a floor, and UV radiation also being directed from the bottom of the device towards the floor.

DETAILED DESCRIPTION

Figure 1:
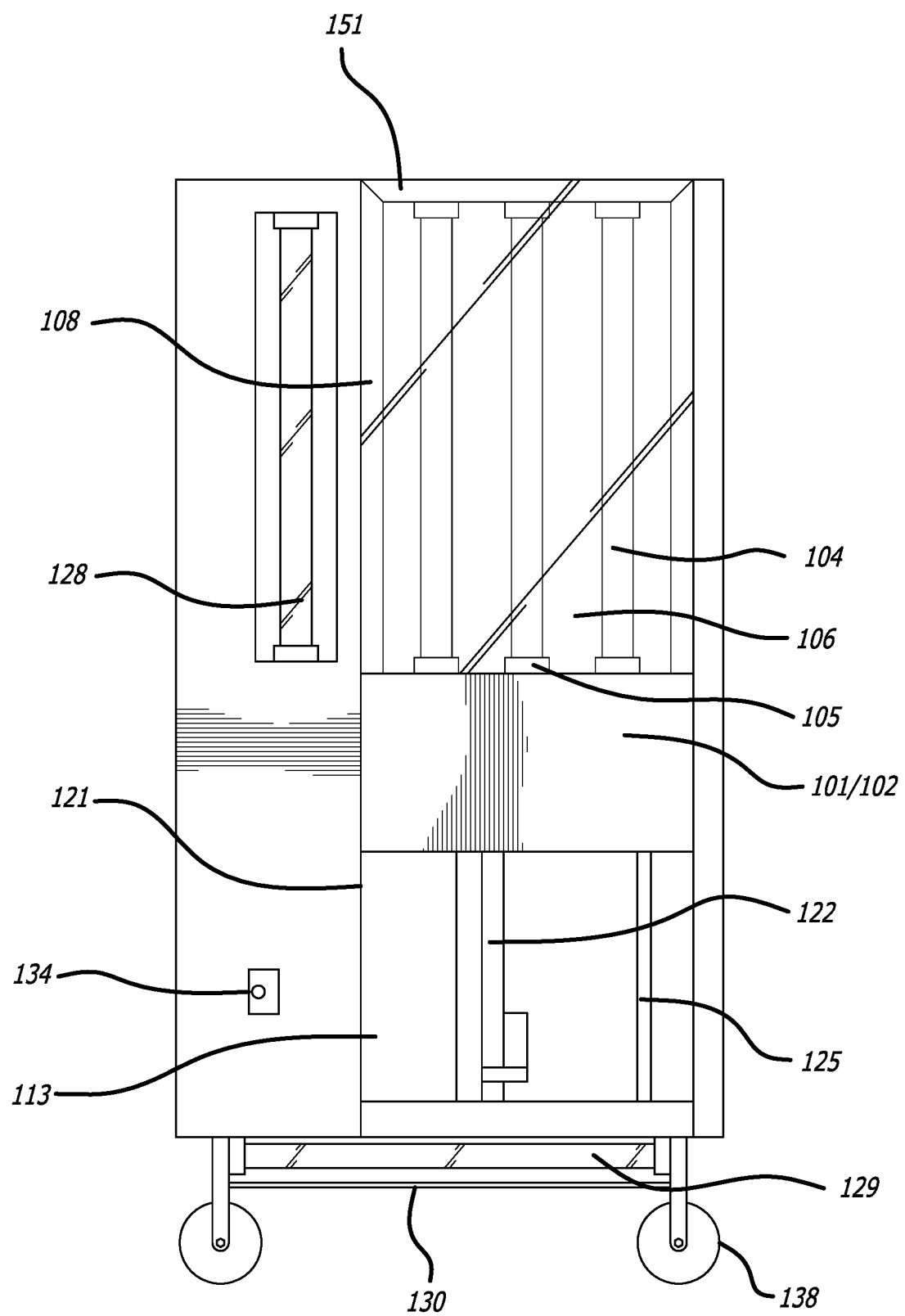
FIG. 1 is a drawing of a right-side view of the sanitation device in transport mode.
Figure 2:
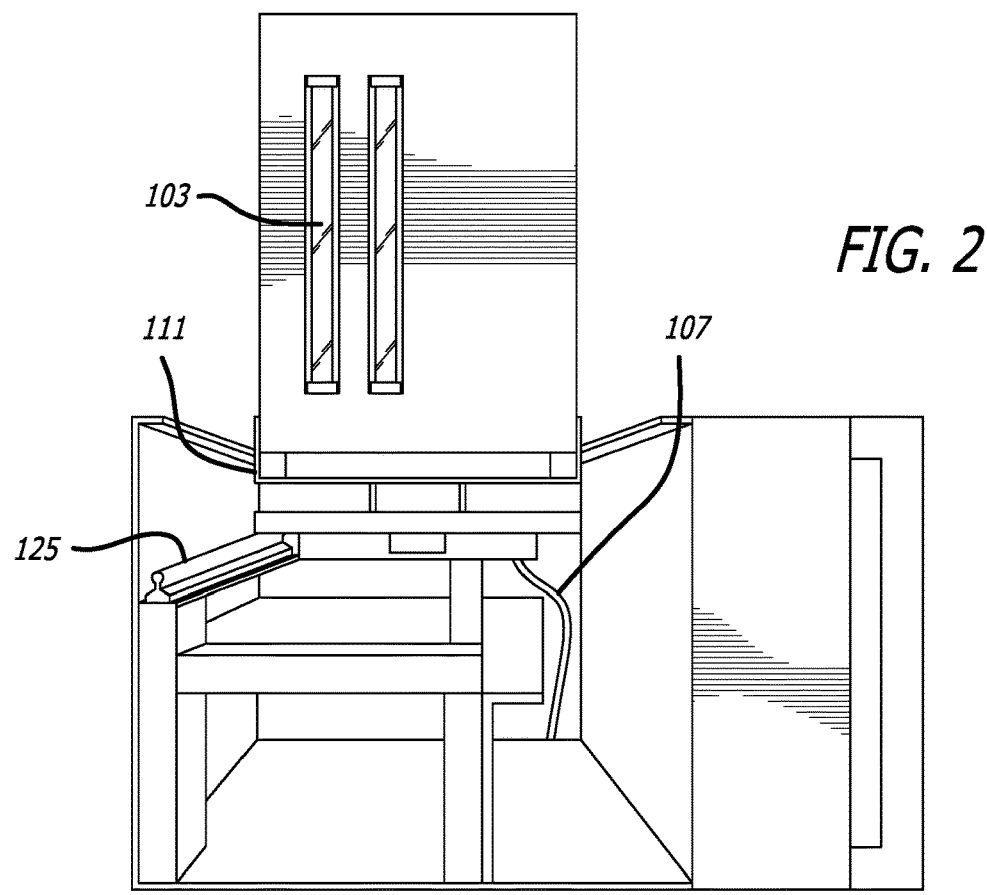
FIG. 2 is a drawing from above of the sanitation device in a floor disinfection mode.
Figure 3:
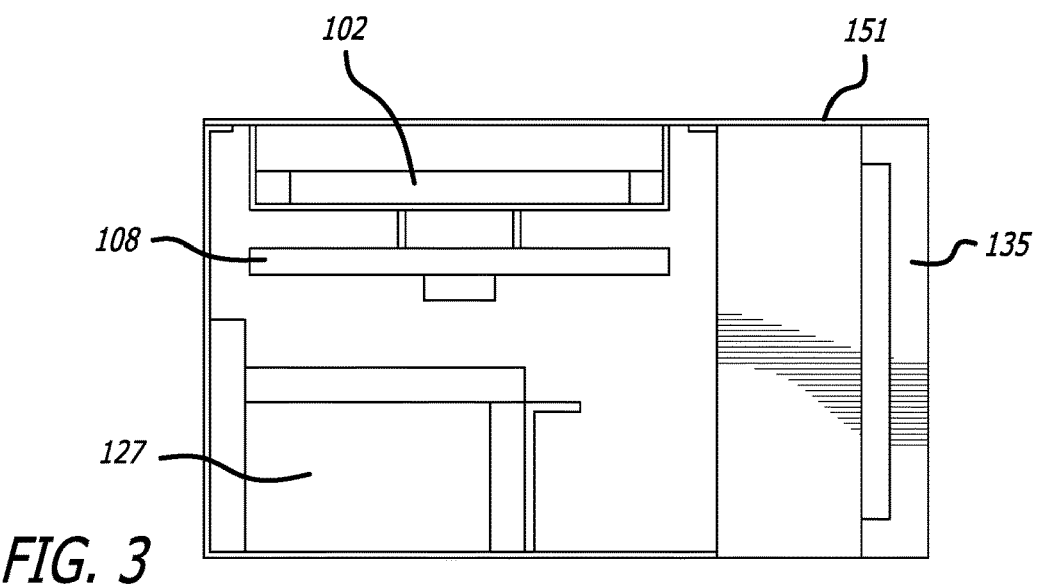
FIG. 3 is a drawing from above view of the sanitation device in transport mode.
Figure 4:
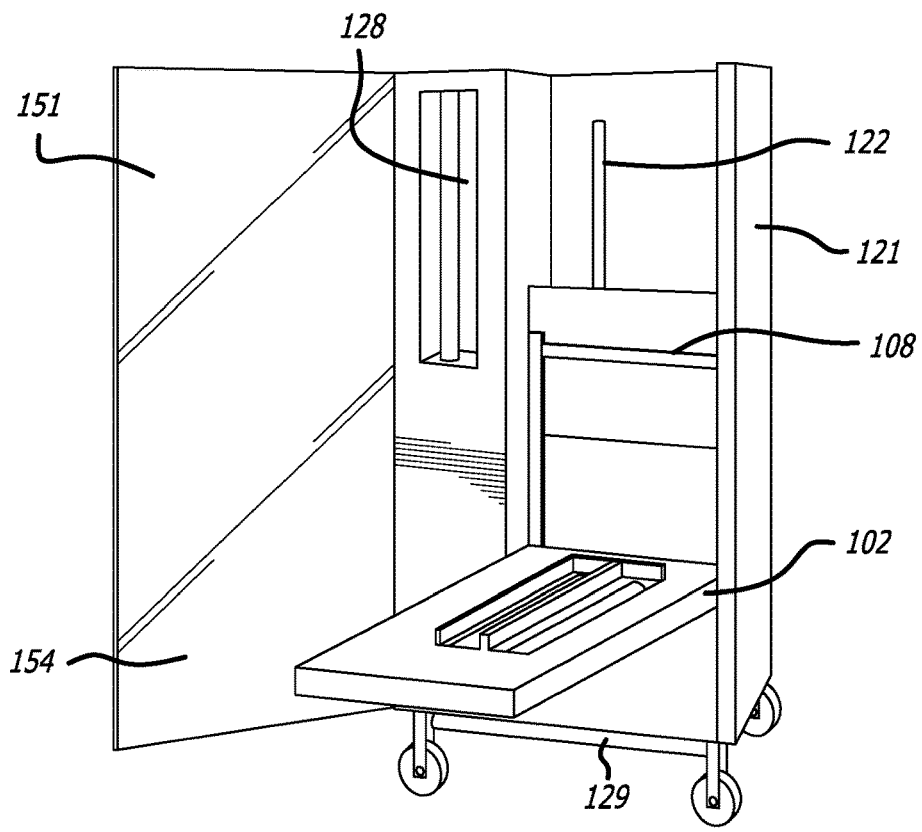
FIG. 4 is a drawing from the side of the sanitation device in a floor disinfection mode.
Figure 5:
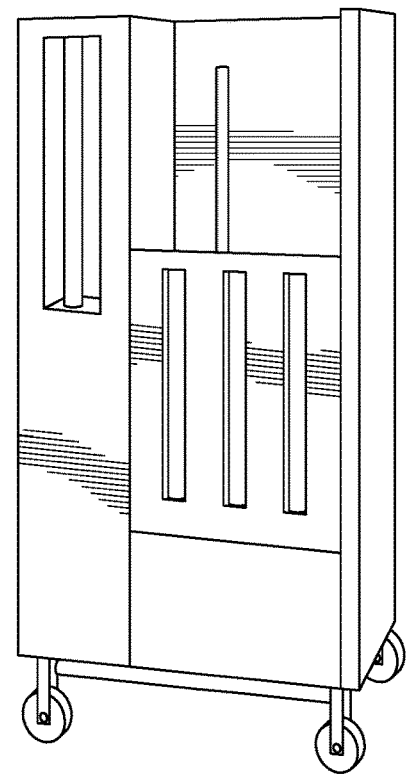
FIG. 5 is a drawing from the side of the sanitation device in a vertical disinfection mode.
Figure 9A:
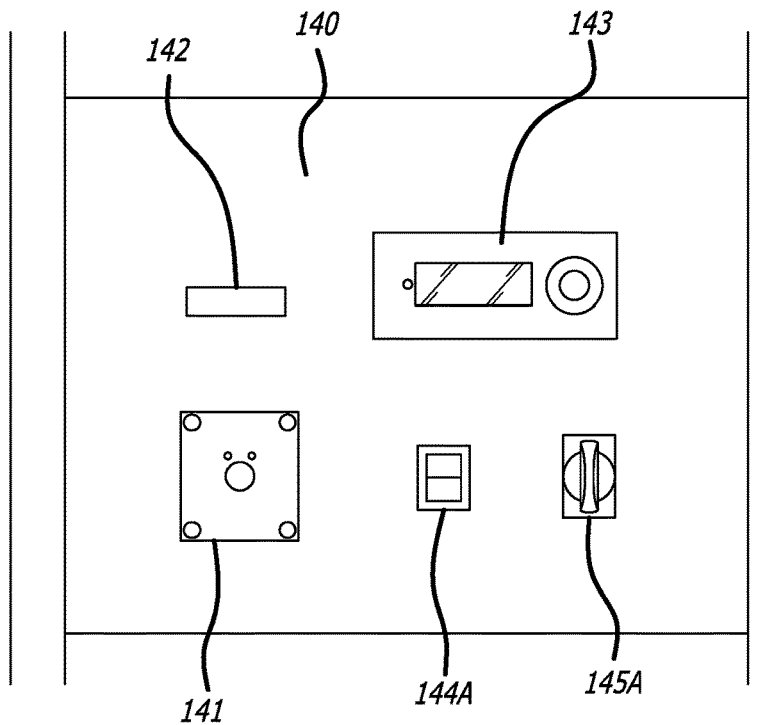
FIGS. 9A and 9B are drawings of the control panel of the sanitation device.
Figure 9B:
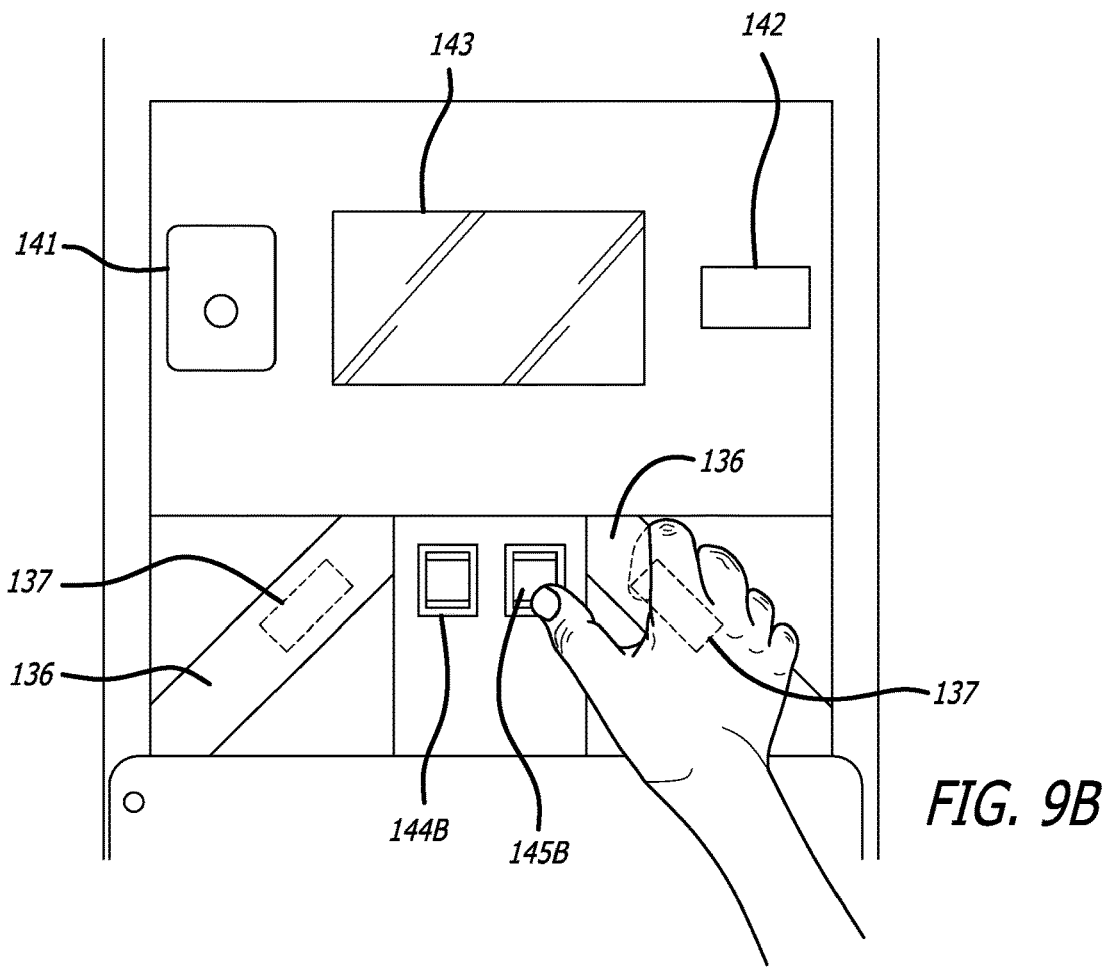
Figure 11:
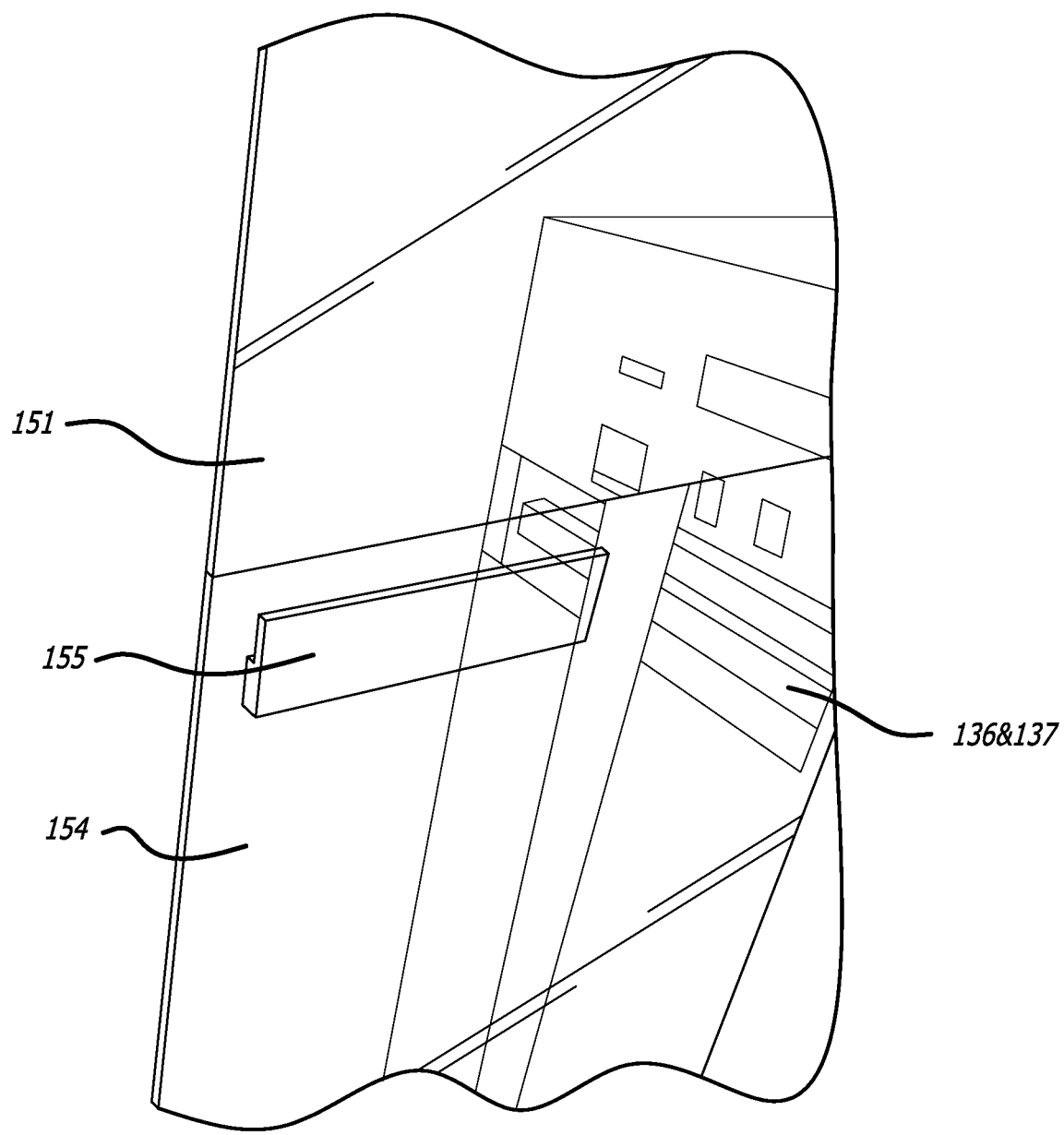
FIG. 11 is a drawing of the sanitation device showing the shield upper and lower sections in mating relationship
Figure 12:
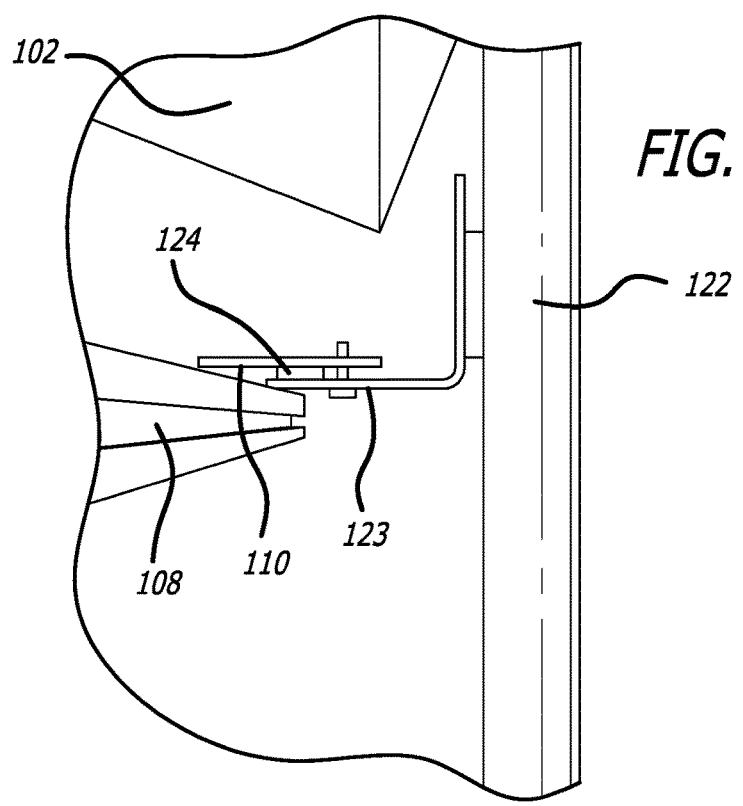
FIG. 12 is a drawing of the sanitation device showing beneath the wing toward the rear.
Figure 13:
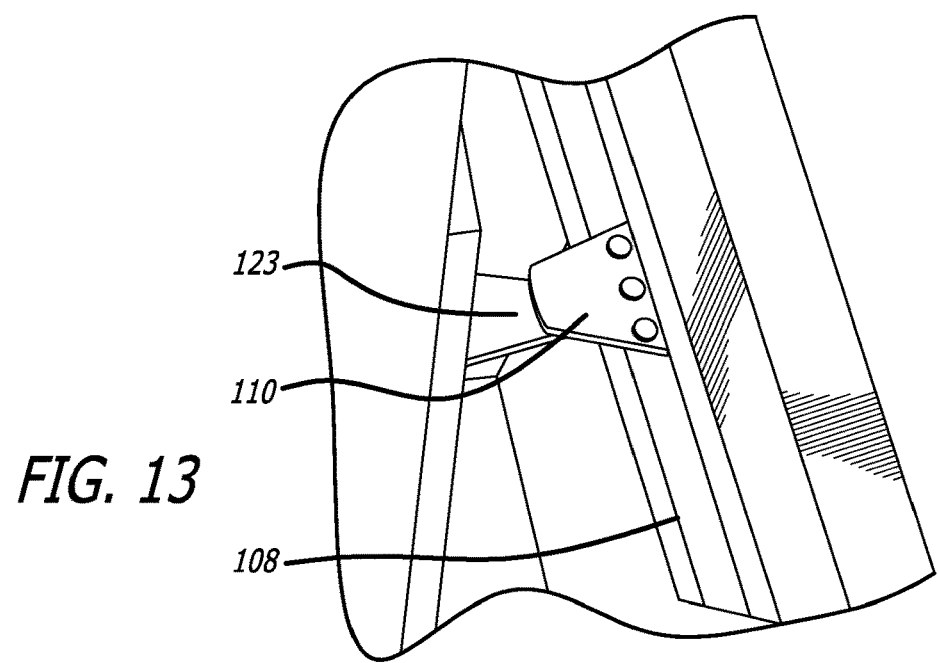
FIG. 13 is a drawing of the sanitation device showing above the wing toward the front.
Figure 14:
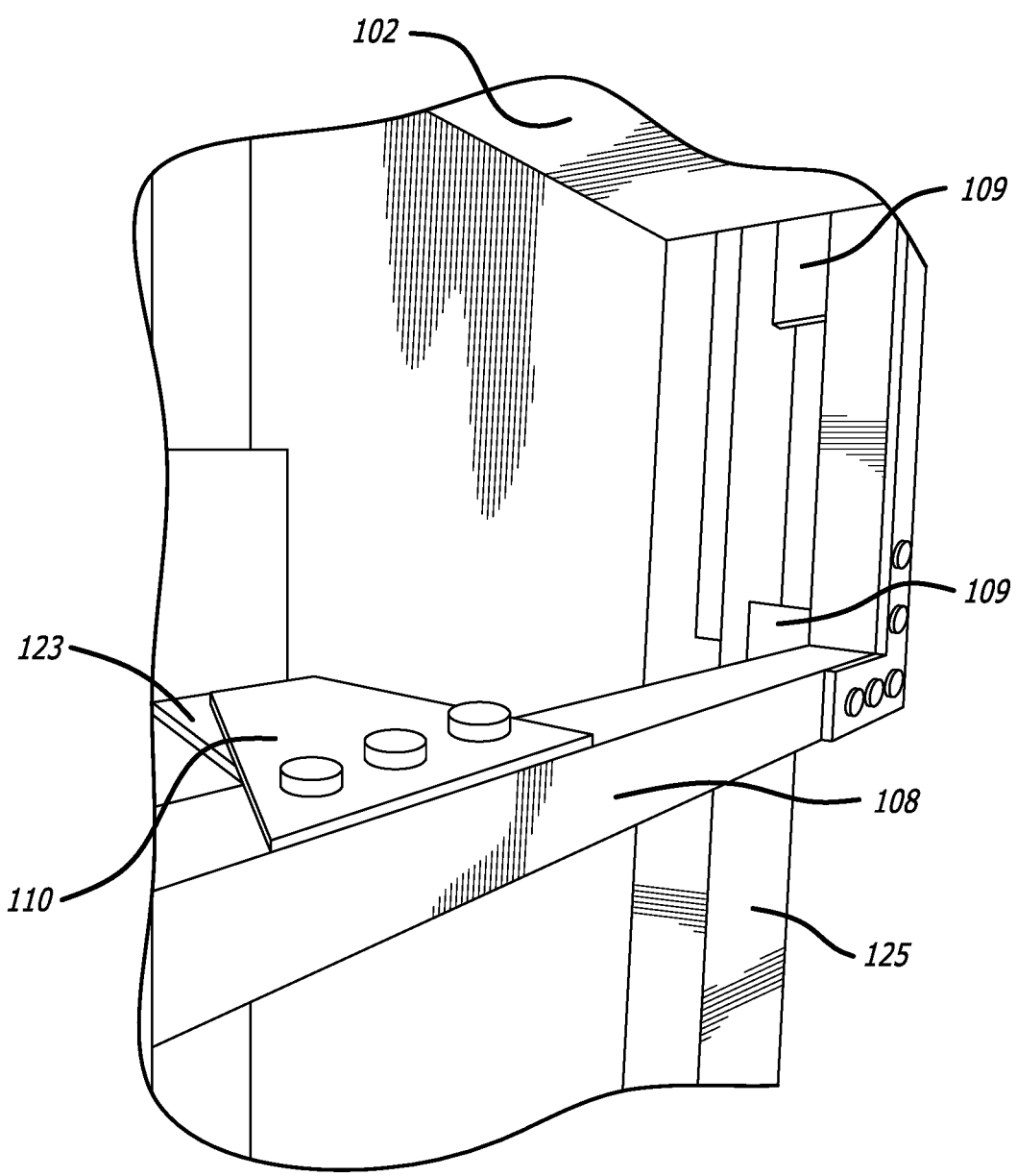
FIG. 14 is a drawing of the sanitation device showing beneath the wing toward the front.
Figure 15:
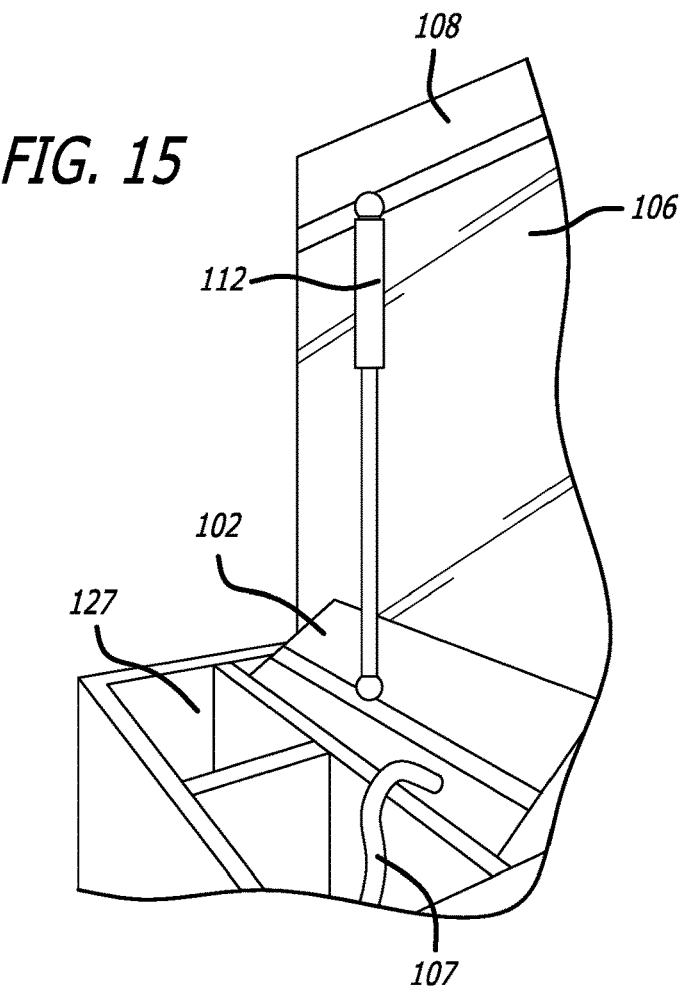
FIG. 15 is a drawing of the sanitation device showing the wing moving to the horizontal from the left side.
Figure 16:
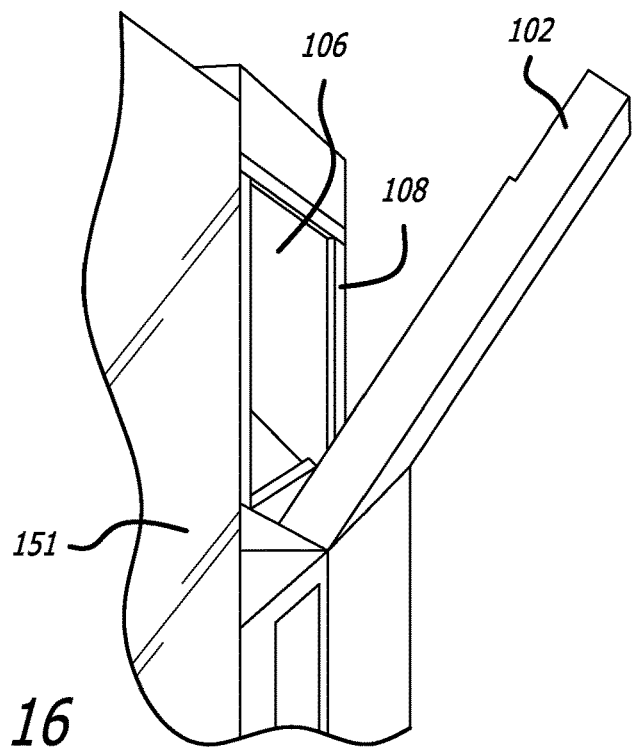
FIG. 16 is a drawing of the sanitation device showing the wing moving to the horizontal from the right side.
Figure 17:
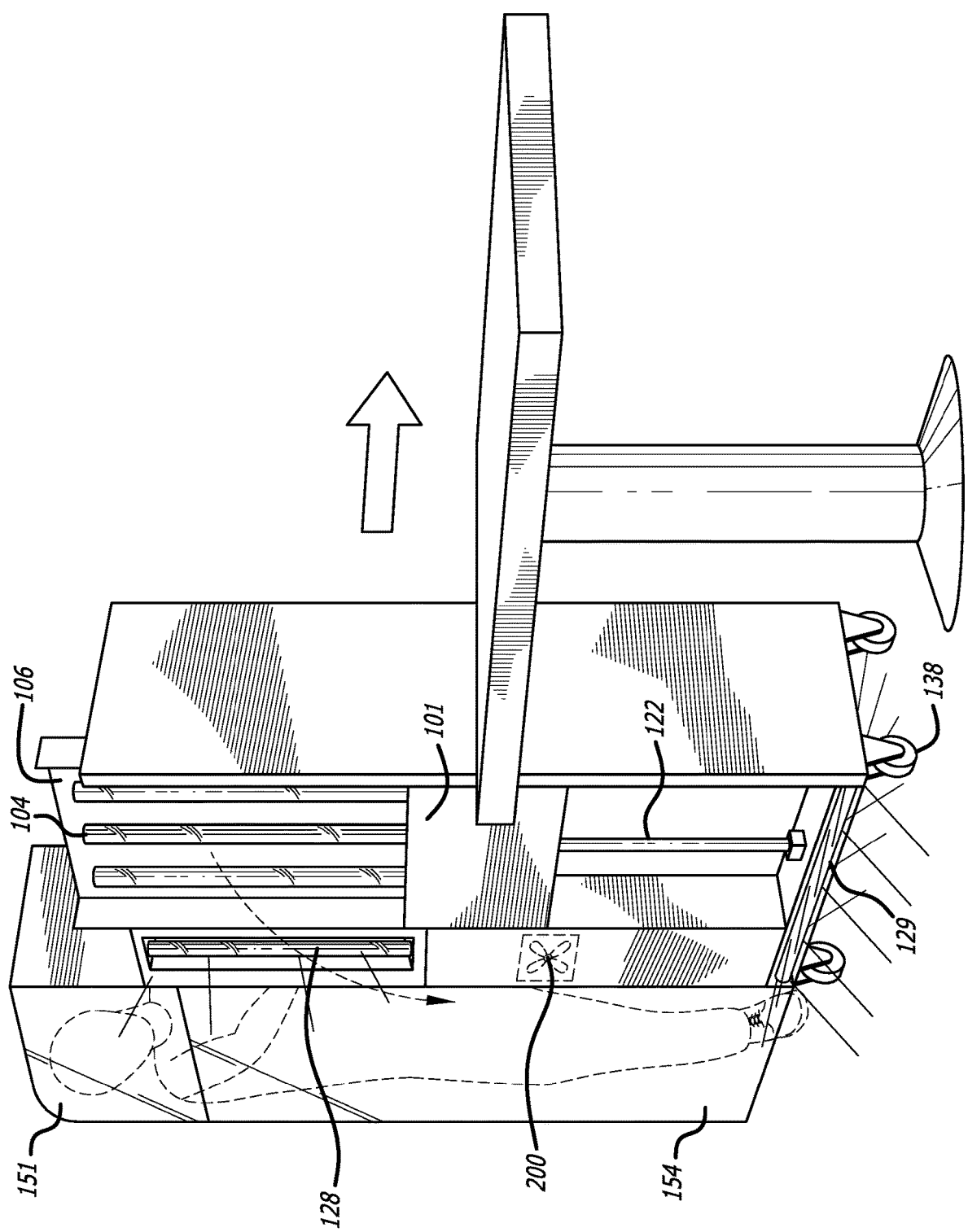
FIG. 17 is a drawing of the sanitation device showing the device in the environment of a hospital with the user protected by the shield and the wing in a vertical raised position prior to movement over a table.
Figure 18:
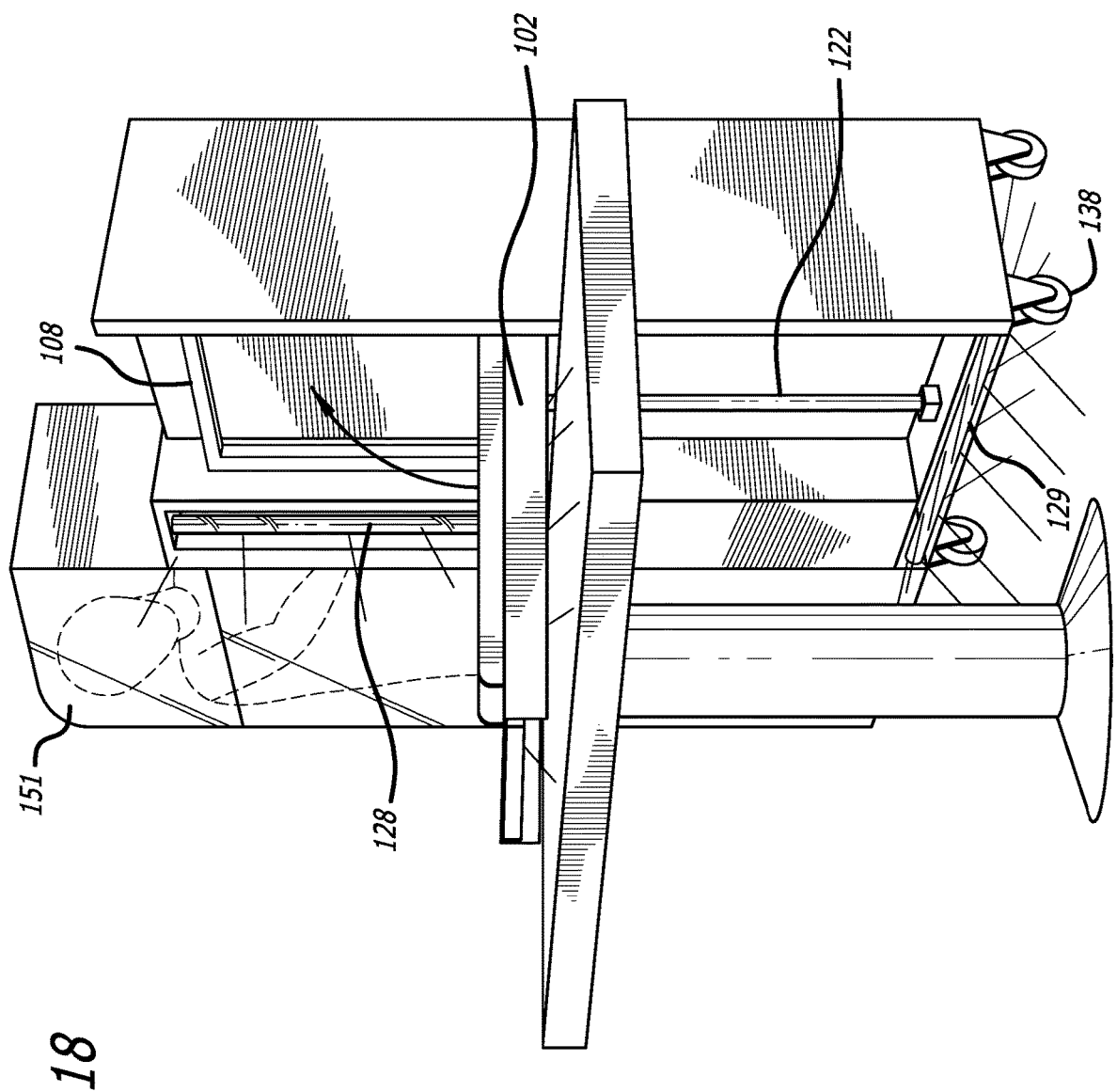
FIG. 18 is a drawing of the sanitation device showing the device in the environment of a hospital with the user protected by the shield and the wing in a horizontal position moving over a table top.
Figure 19:
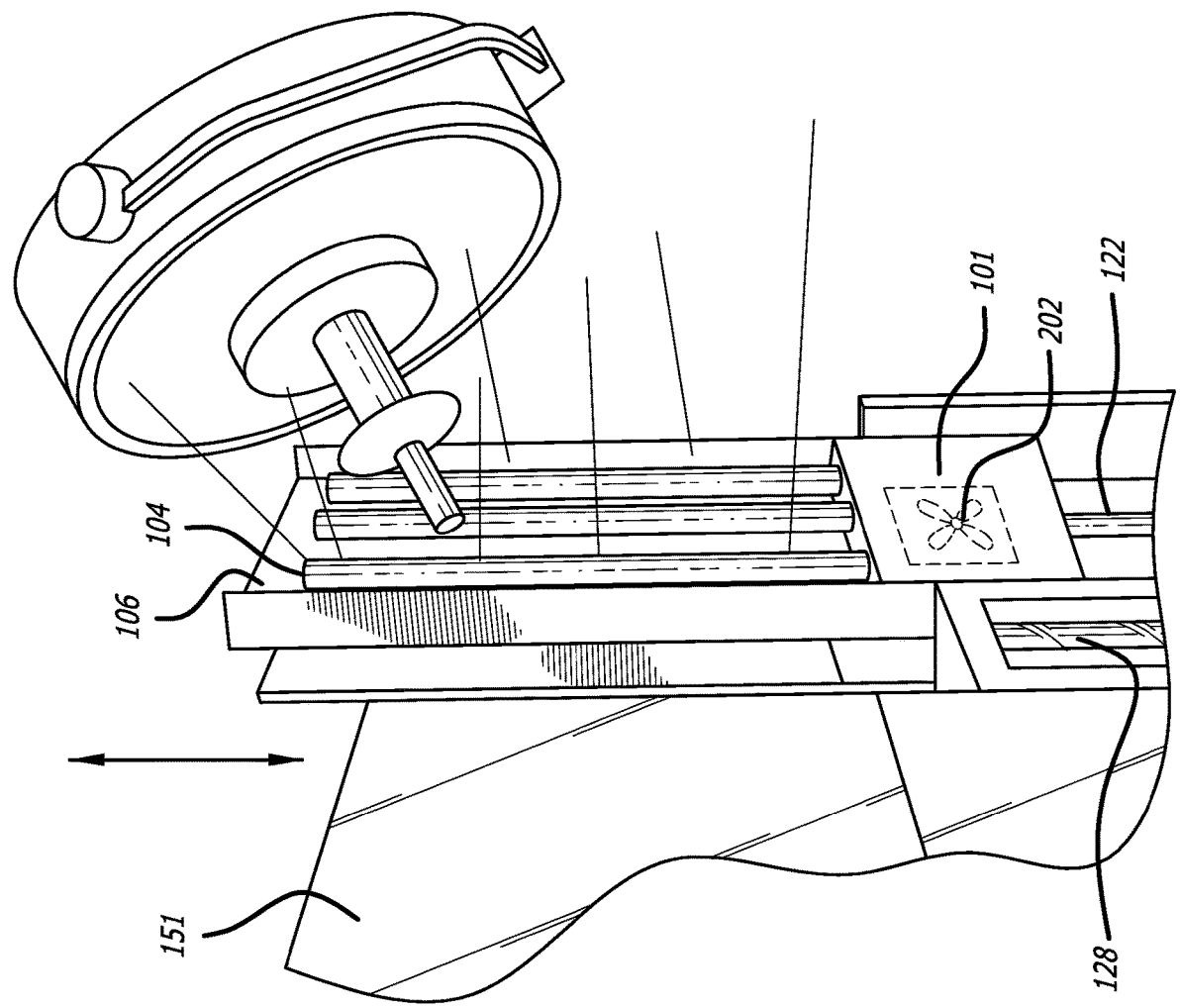
FIG. 19 is a drawing of the sanitation device showing the device in the environment of a hospital and the wing in a vertical raised position relative to a light.
Figure 20:
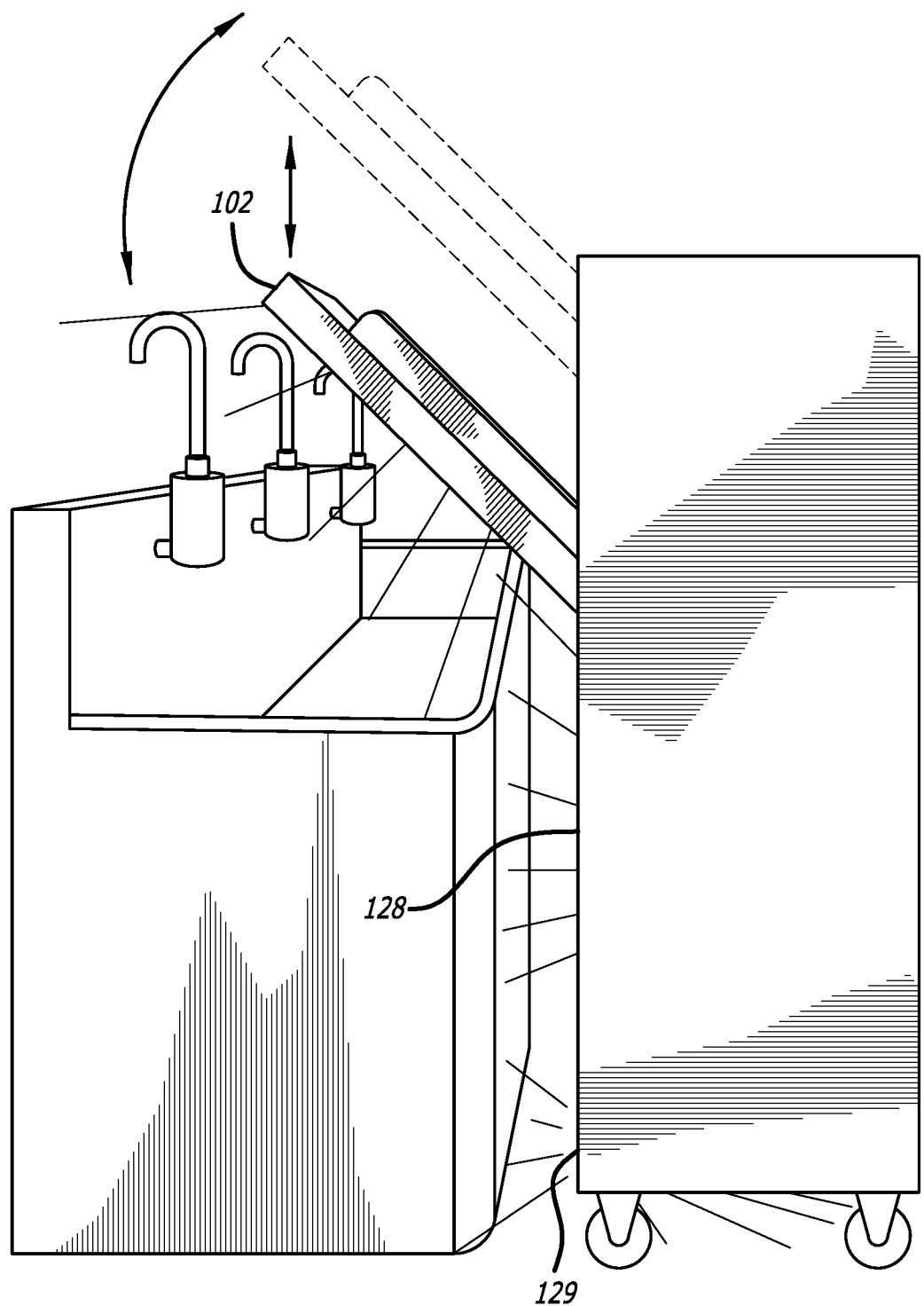
FIG. 20 is a drawing of the sanitation device showing the device in the environment of a hospital and the wing in an angular position over faucets.
Figure 21:
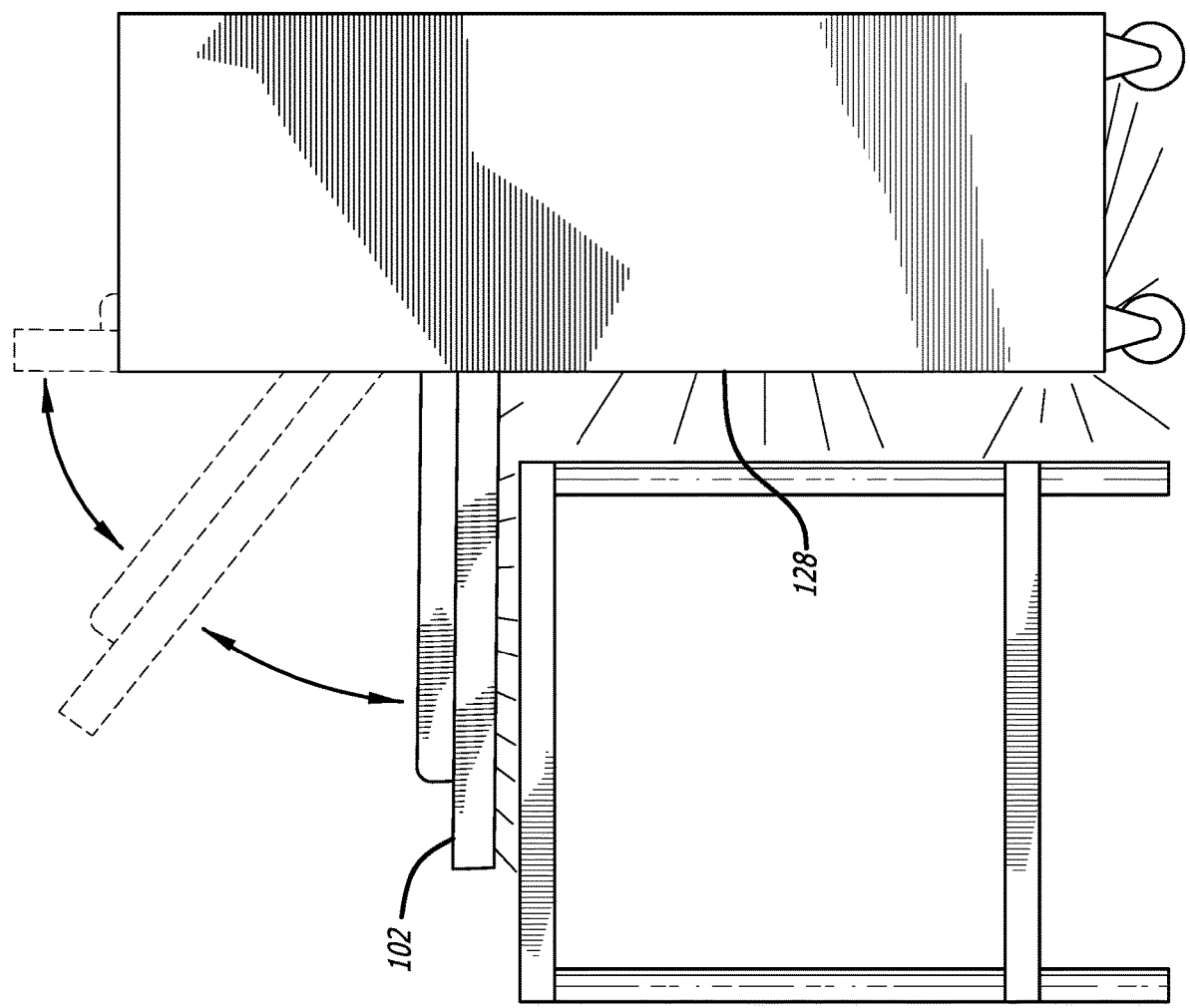
FIG. 21 is a drawing of the sanitation device showing the device in the environment of a hospital and the wing being movable from a vertical through and angular position a horizontal position over a table, and UV radiation also being directed from the bottom of the device towards bottom of the table.
Figure 22:
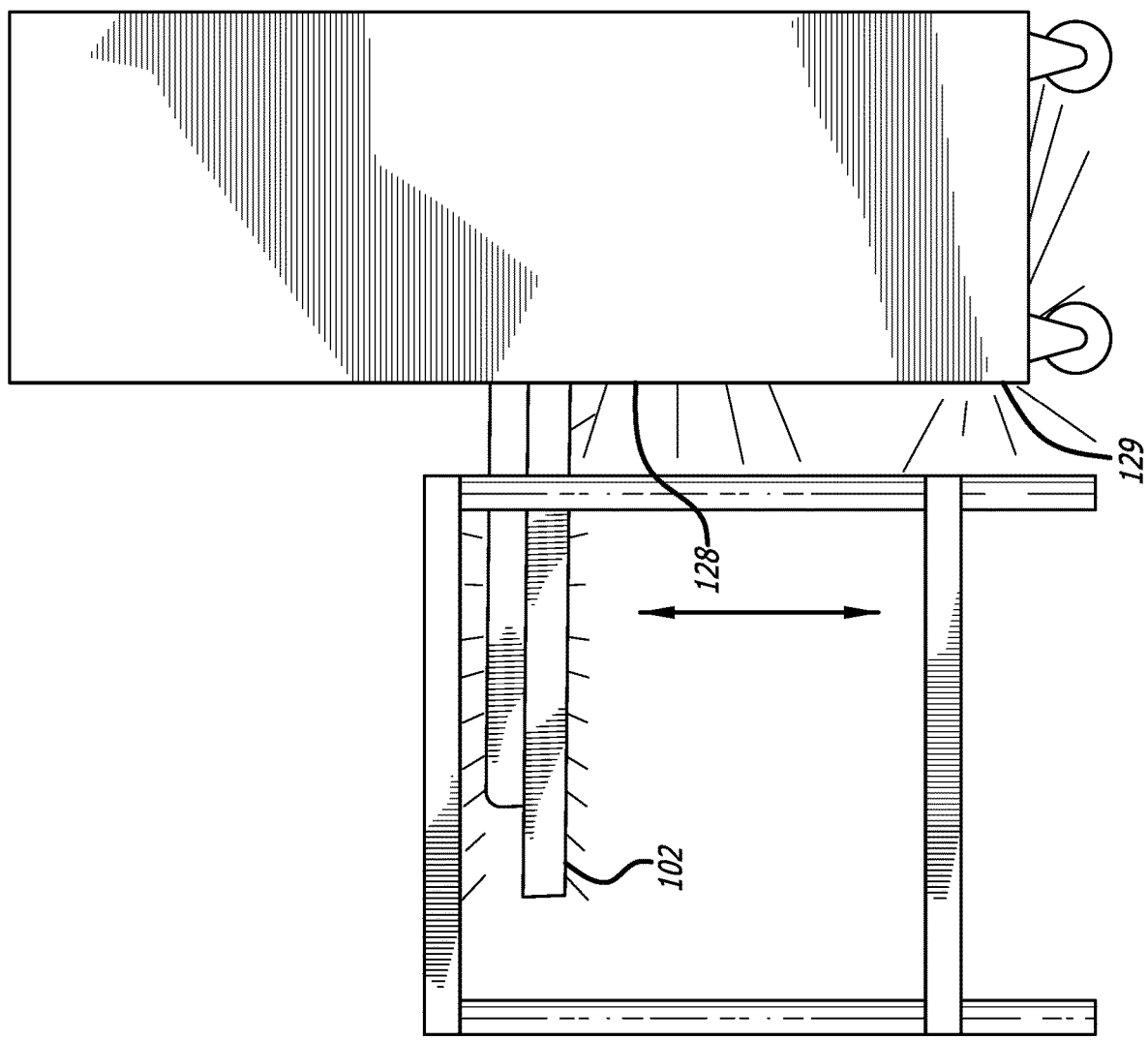
FIG. 22 is a drawing of the sanitation device showing the device in the environment of a hospital and the wing in a horizontal position under an upper level table top with radiation being directed upwardly and downwardly from the wing, and UV radiation also being directed from the bottom of the device towards bottom of the table.
Figure 23:
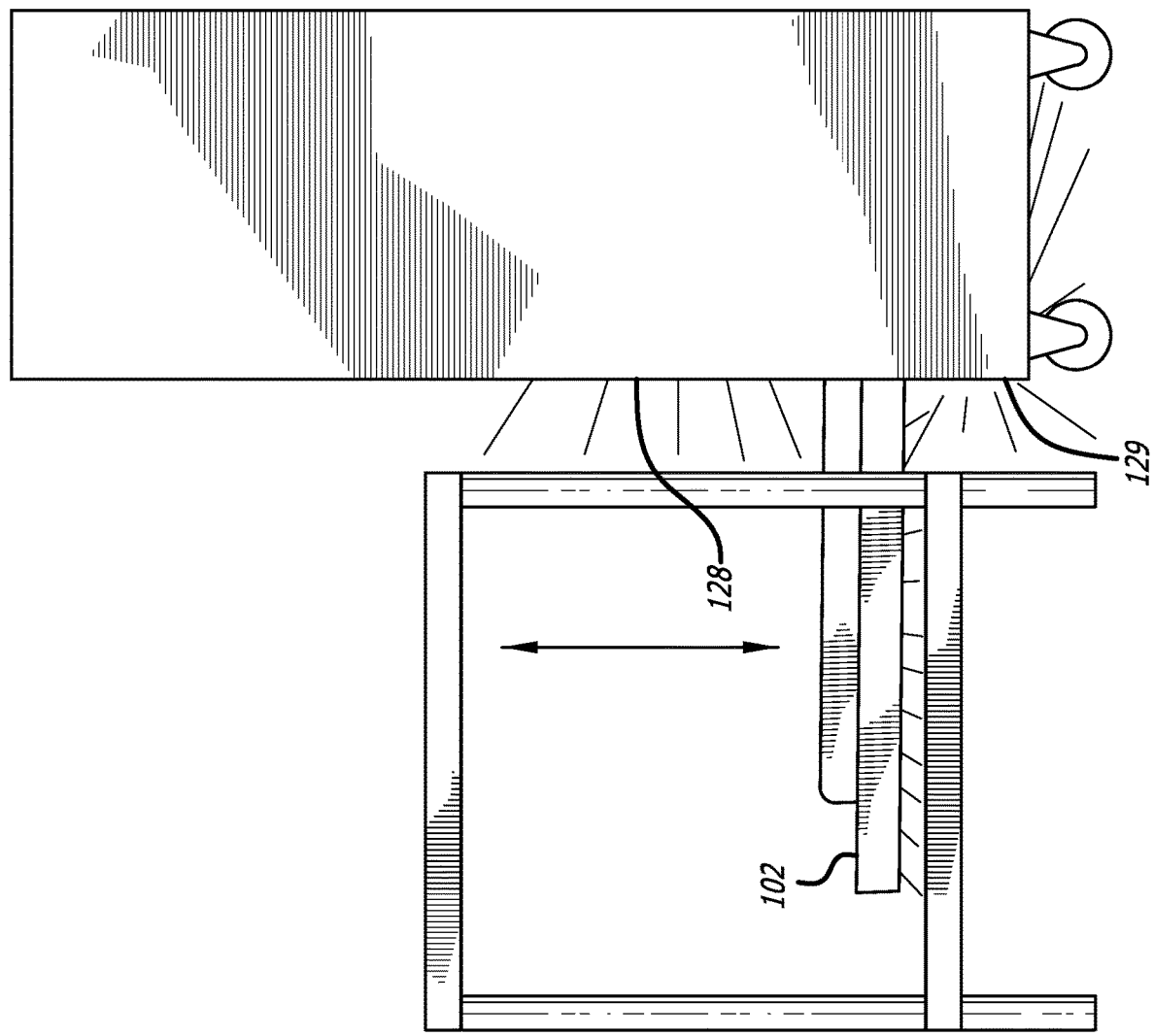
FIG. 23 is a drawing of the sanitation device showing the device in the environment of a hospital and the wing in a horizontal position moved downwardly to be over a lower surface of a table with radiation being directed downwardly from the wing, and UV radiation also being directed from the bottom of the device towards bottom of the table.
Figure 25:
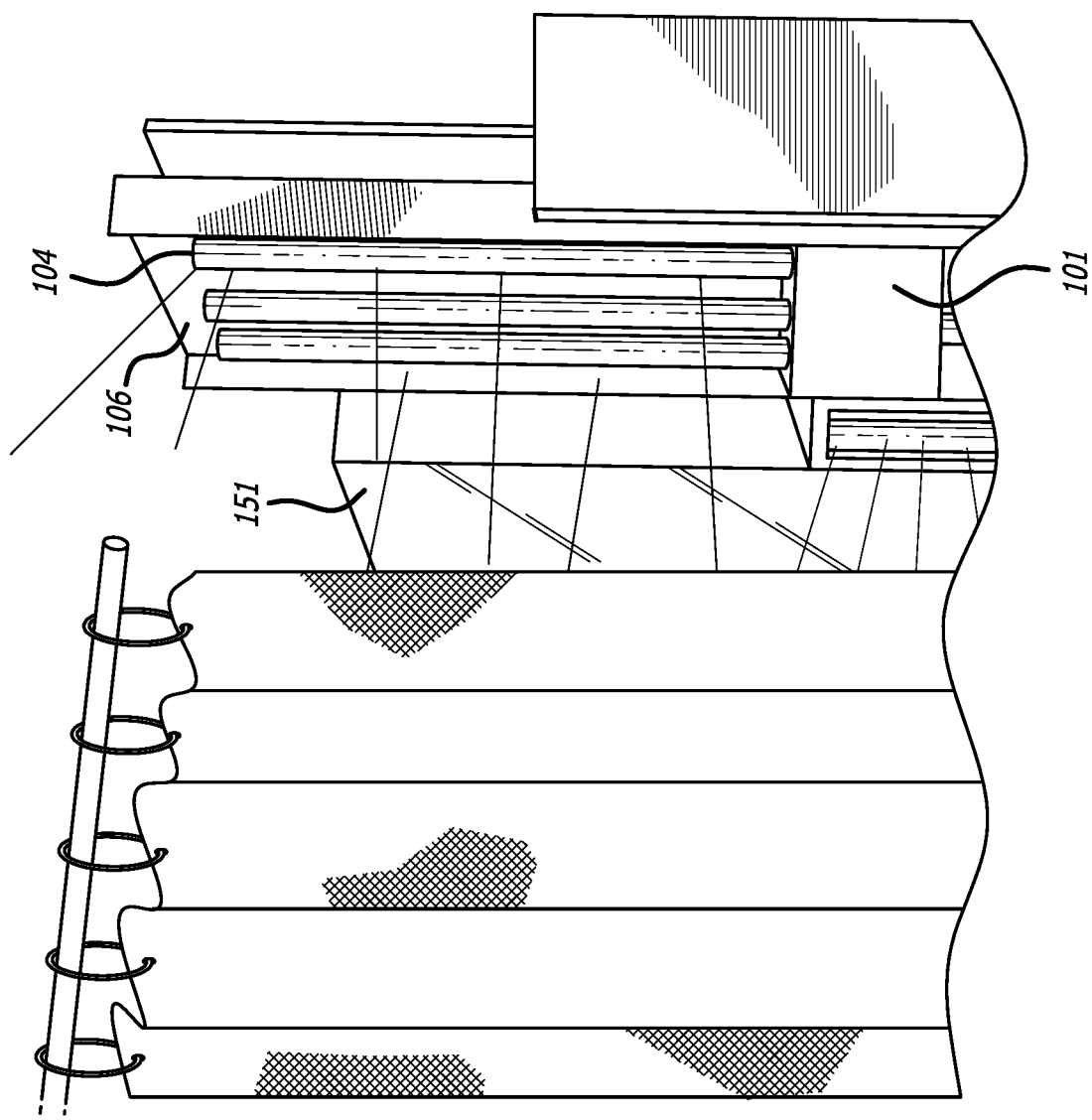
FIG. 25 is a drawing of the sanitation device showing the device in the environment of a hospital and the wing in a vertical position with radiation being extended horizontally from the wing on to a wall and curtains.

The disclosure includes both a method of operation and apparatus for performing the operation.

A method of sanitizing surfaces with apparatus includes the steps of: a) providing a sanitization device including a mobile body; b) extending the sanitization device laterally from the mobile body across a surface, a source of UV radiation being mounted on the sanitization device; c) moving the sanitization device across the surface; d) exposing the surface to UV radiation produced by the source; e) moving the mobile body while the device moves over the surface; f) directing a source of UV radiation to the surface at a predetermined dosage while the device moves over surface; the mobile body being powered by a power source on board the mobile device.

The apparatus is an oblong rectangular-like structure and the sanitation device is in nonuse housed essentially within the bounds of the oblong structure. In use the sanitation device is extended upwardly from the oblong structure, and then deployed into different operative positions relative to the surface to be treated.

The sanitation device is also movable inwardly and outwardly relative to the mobile body across the surface while effecting the sanitation.

The apparatus permits for moving and locating the sanitization device inwardly and outwardly relative to the mobile body to extend at different angles being from a horizontal angle relative to the mobile body to a non-horizontal angle relative to the mobile body and to effect sanitization when so extended.

The device can also operate so that the sanitation device can move upwardly and downwardly across the surface while effecting the sanitation.

In one form there is only a single sanitation device mounted on a single side of the mobile device. The remaining sides of the mobile device being either a closed panel or having a utility door panel. In this configuration the method and apparatus and system consists as having a single sanitation device, or a single movable arm, or a sanitation device mounted on a single side, or a single sanitation device mounted for lateral movement and displacement on a single side.

A structure for mounting the UV radiation source is arranged to run relatively vertically in a track upwardly or downwardly and a telescopic arm is provided to direct the structure into and out of the track, so as to adopt different angles relative to the horizontal or vertical relationship. The structure is essentially a movable wing mounted on the mobile housing so that the UV radiation source is visible or exposed as part of the side wall of the housing when not in use or when in use located in its vertical mode. The track actuator or telescopic arm is mounted from the base of the mobile device vertically upwards, and the structure can slide upwardly and downwardly in a track located on the housing. There can be two vertical tracks, one to either side of the structure for locating the structure to move positively in the mobile device. Other parts of the side wall can locate one or more lamps.

The movable wing is such that it can be directed horizontally. The height of the horizontally positioned wing can be independently adjusted from a very low level to disinfect the floor and very high to disinfect a tall shelf. The height of the wing in the horizontal position can be further and finely adjusted to place the wing in very close proximity to the target surface. The wing can also be directed vertically, and at any angle between horizontal and vertical. A vertical surface can be disinfected by independently adjusting the height the wing in the vertical position. This includes flexible vertical surfaces such as a curtain with its folds. With the wing in the vertical position, the base is moved to bring the lamps into very close proximity to the vertical surface. A sensor can establish the optimal degree of adjacency to provide for effective and efficient use. The sensor can also prevent the wing movement from engaging a surface and can be of a kind that as the surface to be cleaned changes in shape automatically moves the wing to appropriate levels, locations, angles and positions. It is considered that an adjacency relative to a flat, for instance a horizontal surface, in the range 0.5 cm to 3 cm and preferably about 1.0 cm would make for effective, timely and efficient sanitation.

A method, system, and apparatus for sanitizing a floor surface includes a sanitization device including a mobile body. The sanitization device is mounted to permit lateral extension from the mobile body across a floor surface. A source of UV radiation being mounted on the sanitization device; the sanitization device being movable across the floor surface to expose the surface to UV radiation produced by the source. The UV radiation is directed to the surface at a predetermined dosage while the device moves over surface. The device is selectively operable upwardly and downwardly across the surface while effecting the sanitation. The movable wing can selectively be directed downwardly horizontally to clean a floor. In the horizontal mode the wing can be in close proximity horizontally and selectively between about 0.5 cm to about 3 cm, and further optionally at about 1 cm adjacent to the horizontal floor surface being cleaned. Optionally a sensor can establish the right degree of adjacency to provide for effective and efficient use.

Further the device can deliver sanitation UV radiation selectively in one or more directions from one or both sides of a structure for mounting the UV source. The UV source can be sheltered, so as to direct the UV radiation in selected directions and not in other directions.

In some forms the UV is directed solely in one orthogonal direction with a defined arc to either side from that direction from the sanitation device panel and not in an opposite orthogonal direction. The UV source on the panel and the sanitation device can be controlled in to be at different predetermined levels relative to the surface to be sanitized.

The disclosure is unique and novel because it capitalizes on the physical properties unique to UV light and turns limitations into advantages.

Because some materials such as polycarbonate, vinyl, glass and acrylic transmit visible light but block UV light, a shield of this material safely permits the operator to be in the room during UV disinfection. This allows for the first time the device that can be manually pushed around the room, bringing the UV source extremely close to the surface to be disinfected, slashing treatment times.

The current disclosure features an operator-controlled system that variably orients the UV sources from vertical to horizontal positions at a wide range of heights. This allows rapid and effective disinfection of both vertical and horizontal surfaces not available with known devices.

Textured surfaces, ubiquitous in the healthcare and other environments, are easily disinfected by the current disclosure because the combination of motion, correct UV source orientation and close proximity to target surface preclude all "hiding places" for pathogens as troughs and valleys are completely exposed to the germicidal UV light.

The best performing known healthcare UV emitting devices are published to achieve bacterial kill rates of 60-75% and requiring more than 20 minutes per patient room. Even with these kill rates, HAIs have been reduced using known devices.

A novel feature of the current disclosure allows documented 99.9% kill rates in as little as 3 minutes per room. This unexpected efficiency is anticipated to dramatically reduce infection transmission to prevent illness and deaths.

The combination of the protective shield for a user with the ability to be in the room to locate the lamps at the optimal location, height and angle relative to the surface, renders the device, system and the method fast and effective. In use in a hospital environment for instance the shielding and structure and action of the wing imparting the UV, translates into not always requiring room evacuation when cleansing is being affected. By not having to leave the room every time the machine is relocated to one of several positions, there is significant time saving.

In a hospital environment, C. Diff, an infectious agent particularly difficult to kill. Prior devices with sufficient UVC delivery to kill requires about 10 minutes from a distance of 4 feet. The disclosed device system and method combining the near proximity, lamps parallel to the target surface and active motion, require an exposure to under 3 seconds—namely completing this task 200 times faster. This would be of great benefit to patients in preventing life threatening infections.

The Disclosure Parts and how they Connect

PARTS LIST

| Part # | Part Name |
|---|---|
| 101 | Wing assembly |
| 102 | Wing |
| 103 | Wing penetrations |
| 104 | Lamp |
| 105 | Socket |
| 106 | Reflective material |
| 107 | Wing wires/plugs |
| 108 | Wing frame |
| 109 | Carriage |
| 110 | Wing frame platform |
| 111 | Wing pivot point |
| 112 | Linear actuator |
| 113 | Ballasts |
| 121 | Base |
| 122 | Track actuator |
| 123 | Track actuator platform |
| 124 | Magnets |
| 125 | Slide |
| 126 | Plug receptors |
| 127 | Storage compartment |
| 128 | Base side lamp |
| 129 | Base floor lamp |
| 130 | Guard for floor lamp |
| 131 | Boot cover compartment |
| 132 | Battery compartment |
| 133 | Circuit breaker |
| 134 | Charger receptor |
| 135 | Transport handlebar |
| 136 | Operation handlebar |
| 137 | Lamp power switch |
| 138 | Wheels |
| 139 | Electronics compartment |
| 140 | Control panel |
| 141 | Main power switch |
| 142 | Battery meter |
| 143 | Speedometer display |
| 144 | Wing up/down control |
| 145 | Wing vertical/horizontal control |
| 151 | Shield upper section |
| 152 | Shield upper section pivot point |
| 153 | Shield retaining magnet |
| 154 | Shield lower section |
| 155 | Shield lower section mating groove |

The disclosure is comprised of two separable components, a wing assembly (101) and a base (121). These components attach mechanically via at least one slide (125) mounted to the base (121) and at least one carriage (109) mounted to the wing frame (108). A track actuator (122) has a track actuator platform (123) that supports a wing frame platform (110) attached by platform magnets (124).

The wing assembly (101) is comprised of the wing (102) attached to the wing frame (108) by wing pivot points (111) and by a linear actuator (112). The preferred location of the actuator mechanism is behind and above the wing. The preferred pivot point is located near the center of gravity of the length of the wing.

The wing contains a plurality of lamps (104) which mate with sockets (105) wired to ballasts (113) to power the lamps (104). The wing (102) is open on the lower surface of the wing (102) to direct lamp (104) output substantially downward when the wing (102) is in the horizontal position and outward when the wing (102) is in the vertical position. Wing penetrations (103) on the upper surface of the wing (102) also allow some lamp (104) output to be directed upward when the wing (102) is in the horizontal position. Reflective material (106) is provided adjacent to and behind the lamps (104) to increase effective lamp output.

The wing (102) contains ballasts (113) located nearer the base (121) that power the lamps (104) on the wing (102). The wing wires/plugs (107) exit the end of the wing (102) nearer the base (121) and power the ballasts (113) and linear actuator (112) and connect to the plug receptors (126) on the base (121).

Carriages (109) are attached to the wing frame (108) that engage at least one slide (125) attached to the base (121). In the preferred embodiment, a frame platform (110) is attached to the lower end of the wing (102) to engage the track actuator (122) attached to the base (121).

The base (121) is on a plurality of wheels (138), at least two of which allow motion of the base in any plane parallel to the floor. Mounted to the base (121) is at least one slide (125) to engage the carriage (109) mounted to the wing frame (108). Mounted to the base is a track actuator (122) oriented in a substantially vertical direction. The track actuator (122) has a track actuator platform (123) with platform magnets (124) to engage the ferrous frame platform (110) of the wing (102). Plug receptors (126) are mounted on the base to accept the wing wires/plugs (107).

The base (121) has a storage compartment (127) with capacity for contents including but not shown, a device cover, a lamp breakage kit, a charger, gloves, a manual, etc.

There is an electronics compartment (139) which contains but not shown, power converters/inverters, ballasts (113) for lamps (104) circuit breakers, wires, plugs, microprocessors, etc. required for device operation.

The base (121) has a boot cover compartment (131) located accessible to the operator with capacity to hold disposable commercially available boot covers. There is a battery compartment (132) with capacity to hold batteries of a variety power storage options depending on operator needs. Located within the battery compartment (132) is a circuit breaker (133) to protect overloads with capability to serve as a master shutoff and emergency shutoff.

The base (121) also contains lamps (104) wired to sockets (105) and ballasts (113) located in an electronics compartment (139). Multiple lamps are provided on the base (121), including a base floor lamp (129) with a guard for the floor lamp (130) to prevent breakage. A base side lamp (130) is strategically located and oriented to provide UV exposure to the vertical surface of a target structure that also has a horizontal surface. The base side lamp (128) sends rays at the target surface. Also, the base floor lamp (129) sends rays to the side as drawn, but also directly onto the floor and onto all 4 wheels (138). The wheels are disinfected so as to not cross contaminate the hallway between rooms or the next room.

Located at the rear top of the base (121) is the transport handlebar (135). An operation handlebar (136) is located below and parallel to the transport handlebar (135) at a convenient height from the floor. The operation handlebar (136) contains depressible lamp power switches (137), one for each hand, of the "momentary on" type that require continuous pressure to complete the circuit and open the circuit when pressure is released.

Above the operation handlebar (136) is a control panel (140) located to be visible and accessible to the operator. The control panel (140) includes displays of battery meter (142) and a speedometer display (143). The control panel has a main power switch (141), a wing up/down control (144) and a wing vertical/horizontal control (145).

Attached to the base (121) is a shield upper section (151) and a shield lower section (154). These sections are made of a material such as polycarbonate which transmits visible light but is impervious to ultraviolet light.

The shield upper section (151) is rotatably attached to the base (121) at an upper section pivot point (152) so that in the up/operational position, the control panel (140) and operation handlebar (136) are accessible and the shield upper section (151) protects the operator from UVC exposure from approximately the shoulders to head. When the upper shield section is in the down/stowed/transport position, the transport handlebar (135) is accessible, while the control panel (140) and operation handlebar (136) are not accessible. In the down/stowed/transport position, the shield upper section (151) provides a physical block to prevent damage to the lamps (104). The upper shield section is maintained in the down/stowed/transport position with a shield retaining magnet (153) that aligns with a ferrous component on the base (121).

The shield lower section (154) is rotatably attached to the base (121) so that in the open/operational position, protects the operator from UVC exposure from approximately the shoulders to the feet. The shield lower section (154) also has a mating groove (155) to capture the lower edge of the shield upper section (151). This mating maintains the shield upper section (151) in the up/operational position and maintains the shield lower section (154) in the open/operational position. In the preferred embodiment, the lower shield section folds onto itself to fit within the footprint of the base (121).

How the Disclosure is Used:

The disclosure is initially in the stowed state, with power off, and the wing (102) in the lowered and vertical position. The device cover, not shown and well known, may be stowed in the storage compartment (127). The shield lower section (154) is folded against the rear of the base (121) and the shield upper section (151) is in the down/stowed/transport position, providing protection to the lamps (104). If the charger, not shown and well known, is attached to the charger receptor (134), it is unplugged for device use. The charger may be stowed in the storage compartment (127).

The disclosure is transported between disinfection sites by pushing and steering via the transport handlebar (135), causing rotation of the wheels (138) and movement of the base (121) to the area to be disinfected. The shield upper section (151) is manually rotated upward into the up/operational position and held with one hand. The shield lower section (154) is rotated to the open/operational position and the mated to the shield upper section (151) by the mating groove (155). The operator dons boot covers from the boot cover compartment (131).

To disinfect a vertically oriented surface, the wing (102) is maintained in the vertical position. The height of the wing assembly (101) is adjusted using the wing up/down control (144) on the control panel (140) to the desired level. Depressing both lamp power switches (137) on the operation handlebar (136) to power the lamps (104), the device is pushed alongside the target surface, staying as close as possible to the target surface. In some circumstances, the device is pulled alongside the surface.

To disinfect a horizontal surface, the wing (102) is rotated to the horizontal position using the wing vertical/horizontal control (145A) on the control panel (140). The wing assembly (101) height is adjusted using the wing up/down control (144A) on the control panel (140) to bring the wing as close to the horizontal surface as possible. Depressing both lamp power switches (137) on the operation handlebar (136) to power the lamps (104), the device is pushed alongside the target surface, staying as close as possible to the target surface. The operational bar 136 has two handles as shown on the new diagram. The switches (144B) and (145B) are operated by thumbs. This allows the operator to adjust the wing without moving the hands or taking the eyes off the target. Bar (136) shows both the handles. A thumb on a hand shows depressing 145B. The lamp power switches (137) are on the backs of the handles so that an index or middle finger could depress it while the thumb does something else. In some circumstances, the device is pulled alongside the surface. The floor is treated as any other horizontal surface with the wing assembly (101) height to its lowest level To disinfect the underside of a horizontal surface, the wing (102) is positioned beneath the horizontal surface, wing below the horizontal surface, and then raised to a level as close to the undersurface as possible. The lamps (104) are then powered on and the device pushed/pulled alongside the horizontal surface. The wing penetrations (103) allow the UV light to disinfect the underside of the horizontal surface. Fans can be located on the base (121) and/or the wing assembly (101) to circulate room air in such a manner that the air is directed to flow within the path of the UV lamps to disinfect the air at the same time as the surfaces. These fans would also serve to maintain a more constant lamp temperature for optimal UV output.

To disinfect a slanted surface, the wing (102) is rotated to an orientation parallel to the target surface and powered on as above.

To disinfect a specific object such as a toilet, the lamps (104) are powered on for a set time, typically less than 3 seconds and then depowered without device motion.

The UVC delivered dose is inversely proportional to device speed. The speedometer display (143) reading assists the operator to be certain adequate dosing is achieved. Some microbes require greater UVC dosing, so speed or exposure time may be slowed and gauged by the speedometer display (143) reading.

The preferred embodiment uses two lamp power switches on the operation handlebar (136) which requires the operator's body to remain protected behind the shield (&) and protected from UVC exposure.

The battery within the battery compartment (132) may be charged by plugging a suitable charger into the charger receptor (134). The battery may also be swapped out within the battery compartment (132) and charged off-board.

The circuit breaker (133) is readily accessible in the battery compartment (132) and serves as protection against electrical overload. It may also be used as an emergency manual shutoff or to completely depower the system for longer term storage.

For some transport and servicing purposes the wing assembly (101) may be removed from the base (121) by unplugging the wing wires/plugs (107), the plug receptors (126) on the base (121). The wing assembly (101) is manually lifted, overcoming the force of the platform magnets (124) holding the track actuator platform (123) to the wing frame platform (110), until the lower carriage (109) is free of the slide (125). The wing assembly (101) may be reengaged with the base by reversing the process.

A comparison is set out between existing systems (referred to as 1st Gen UVC devices) and the disclosed device and method (referred to as a UV-Hammer).

| UV HAMMER ADVANTAGES OVER GEN1 DEVICES | | |
| --- | --- | --- |
| Feature | 1st Gen UVC Devices | UV-Hammer |
| Treatment Time <5 minutes | NO | YES |
| Variable Lamp Orientation (vertical to horizontal) | NO | YES |
| Curtains Disinfected | NO | YES |
| Fabric/Textured Surfaces Disinfected | NO | YES |
| Floor Disinfected | NO | YES |
| Bathroom Disinfected | NO | YES |
| Shoe Covers on Board (prevents cross contamination) | NO | YES |
| Cordless (trip hazard & prevents cross contamination) | NO | YES |
| Practical for patient rooms, ICU, OR, and ER | NO | YES |
| Hospital Cost Analysis | | |
| Treatment Time per room | 40-60 minutes | 5 minutes |
| # Rooms Disinfected per unit/8-hour shift | 7-10 | ~80 |
| # units for 80 rooms/shift | 10 | 1 |

Alternative Embodiments

While our above description contains many specificities, these should not be construed as limitations on the scope, but rather as an exemplification of several embodiments thereof. Many other variations are possible. For example, While germicidal light, with peak effectiveness at 254 nm wavelength is most commonly used, other wavelengths of light, including multiple wavelengths may be employed by this device. Additional alternatives include electrostatic, chemical or other means of germicidal substance applied in the environment.

While the preferred embodiment involves a single short wing, it is possible to add one or more additional wings or other extensions or wings of varying segments and lengths to achieve the same or amplified results. Additional, modified and duplicated shields could be required.

If a "safe" chemical, substance, or light is utilized with the specified invention, the shield could be eliminated.

Although linear actuators and slides are illustrated, motorized slides and other motion/guide devices well known to those skilled in the art are anticipated to achieve the same effect of height and wing orientation variation.

Fluorescent lamps are shown in the specification only for convenience. Alternative means of generating germicidal light or substance are anticipated, including but not limited to xenon, LED and other emerging technologies.

The specification refers to an operator driven device. It is anticipated that a partially or fully autonomous device can achieve the same objectives of placing UV sources near and parallel to the target surface. An operator-free device would require programming, artificial intelligence, sensors, motors and other devices and could eliminate the need for the shield described in the specification.

The wheels in the specification are robotic omniwheels, but alternative wheel configurations, including pivoting casters, could be used to achieve the same maneuverability described.

Software added to the device allows monitoring of such parameters as time of use, location of use, path mapping and other features not described.

It is preferred that a trained operator be utilized for this device for safety to the operator and others. To ensure only qualified personnel use the device, a code or biometric identification device such as retinal or fingerprint scanner could be required to operate the device.

In some different embodiments, the track can be mounted at a non-vertical angle relative to the mobile body, and the track can thereby permit the structure to move inwardly and outwardly from the mobile device at a different angle the mobile body. The sanitation device can in these structures still adopt varying angular positions relative to the track.

Accordingly, the scope should be determined not by the embodiments illustrated, but by the appended claims and their legal equivalents.

Many different formats are possible for the disclosure. It is therefore to be understood that within the scope of the appended claims the disclosure may be practiced otherwise than as specifically described.

What is claimed is:

1. A method of sanitizing surfaces comprising the steps of:
    a) providing a sanitization device including a mobile body;
    b) extending the sanitization device laterally from the mobile body across a surface, a UV radiation source being mounted on the sanitization device;
    c) moving the sanitization device across the surface;
    d) exposing the surface to UV radiation produced by the source;
    e) moving the mobile body while the device moves over the surface;
    f) directing the UV radiation source to the surface at a predetermined dosage while the device moves over surface;
    g) moving and locating the sanitization device under motorized action to extend at a horizontal angle relative to the mobile body and a horizontal surface to be sanitized and to effect sanitization when so extended, and effecting sanitation while the mobile body is moving relative to the horizontal surface being sanitized;
h) moving the sanitation device under motorized action in a track in the mobile body to permit movement in a vertical position upwardly and downwardly;
i) operating the sanitation device to permit the sanitation device to move under motorized action from the vertical position to the horizontal angle, while being located in the track;
k) operating the sanitation device to permit the sanitation device to be movable under motorized action at different angular positions between the vertical position to the horizontal angle while being located in the track, and
l) the UV radiation source being operable to direct and effect UV radiation at the surface to be sanitized in the vertical position, horizontal position and different angular positions.

2. The method as claimed in claim 1 wherein the sanitation device is movable inwardly and outwardly at different angles under motorized action relative to the mobile body across the surface while effecting the sanitation—and wherein the device is operable under motorized action upwardly and downwardly across the surface while effecting the sanitation.

3. The method as claimed in claim 1 for moving and locating the sanitization device under motorized action inwardly and outwardly relative to the mobile body to extend at different angles being from a horizontal angle position relative to the mobile body and to the surface being sanitized when in the horizontal angle position to a non-horizontal angle position relative to the mobile body and to the surface being sanitized and to direct and effect sanitization when so extended relative to the surface being sanitized.

4. The method as claimed in claim 1 operable so that the sanitation device can move under motorized action upwardly and downwardly across the surface while directing and effecting the sanitation.

5. The method as claimed in claim 1 wherein the UV radiation source is arranged to run relatively vertically under motorized action in a track upwardly or downwardly and an arm is provided to direct the UV radiation source from the track so that the UV radiation source is enabled to adopt different angles relative to the horizontal or vertical relationship.

6. The method as claimed in claim 1 for delivering UV radiation from both sides of a structure for mounting the UV source, such that when the radiation source is in a non-vertical position relative to the mobile body, the UV radiation can be directed in both upwardly or downwardly directions, such that when directed upwardly an under portion of the surface receives the UV radiation from the UV source.

7. A method of sanitizing surfaces comprising the steps of:
a) providing a sanitization device including a mobile body;
b) extending the sanitization device laterally from the mobile body across a surface, a UV radiation source being mounted on the sanitization device;
c) moving the sanitization device across the surface;
d) exposing the surface to UV radiation produced by the source;
e) moving the mobile body while the device moves over the surface;
f) directing the UV radiation source to the surface at a predetermined dosage while the device moves over surface;
g) moving and locating the sanitization device under motorized action to extend at a horizontal angle relative to the mobile body and a horizontal surface to be sanitized and to effect sanitization when so extended, and effecting sanitation while the mobile body is moving relative to the horizontal surface being sanitized;
h) moving the sanitation device under motorized action in a track in the mobile body to permit movement in a vertical position upwardly and downwardly;
i) operating the sanitation device to permit the sanitation device to move under motorized action from the vertical position to the horizontal angle, while being located in the track;
k) operating the sanitation device to permit the sanitation device to be movable under motorized action at different angular positions between the vertical position to the horizontal angle while being located in the track,
l) the UV radiation source being operable to direct and effect UV radiation at the surface to be sanitized in the vertical position, horizontal position and different angular positions; and
m) the track permitting the UV radiation source to move under motorized action inwardly and outwardly in the track relative to the mobile device at a different angle the mobile body, and permitting the UV radiation source to adopt varying angular positions under motorized action relative to the track, including switching a first actuator to move under motorized action a wing assembly, being a frame and a wing, in the track upwardly and downwardly vertically, and operating a second actuator to permit the wing to move under motorized action from the vertical position to the horizontal position and to selected angular positions between the vertical position and horizontal position, while the frame remains in the vertical position.

8. A method as claimed in claim 1 and disposing a protective shield for a user with the ability to be in a surgery room to locate the UV radiation at the optimal location, height and angle relative to the surface thereby in use in a hospital environment being the surgery room containing a surgery bed and surgery equipment, the shielding and structure and action imparts the UV radiation without requiring room evacuation when cleansing is affected.

9. The method as claimed in claim 1 for sanitizing a floor surface; the device being selectively operable under motorized action upwardly and downwardly across the floor surface while effecting the sanitation, a wing movably directed downwardly under motorized action to clean the floor, and in the horizontal angle the wing being disposable horizontally, and optionally a sensor for establishing a degree of adjacency to the floor to provide for effective and efficient use.

10. The method as claimed in claim 9 wherein the wing is disposable in proximity horizontally selectively between about 0.5 cm to about 3 cm, and further optionally at about 1 cm adjacent to the horizontal floor surface being cleaned.

11. The method as claimed in claim 1 wherein the sanitation source is operable under motorized action upwardly and downwardly across the surface while effecting the sanitation, moving a wing that mounts the sanitation source under motorized action such that the sanitation source is selectively directed downwardly horizontally to sanitize a floor, or directed vertically to sanitize flexible vertical surfaces with folds, and in the horizontal mode the device is selectively in close proximity horizontally and adjacent to the horizontal surface being sanitized, and in the vertical mode is in a close proximity arrangement to sanitize the flexible vertical surfaces with folds, and optionally a sensor for establishing the degree of adjacency to provide for effective and efficient use.

12. The method as claimed in claim 7 for delivering UV radiation from opposite sides of a structure for mounting the UV source, such that when the radiation source is in a non-vertical position relative to the mobile body, the UV radiation can be directed in both of upwardly and downwardly directions such that when directed upwardly an under portion of the surface receives the UV radiation from the UV source.

13. The method as claimed in claim 6 wherein the UV source is directed upwardly and downwardly at the same time.

14. The method as claimed in claim 12 wherein the UV source is directed upwardly and downwardly at the same time.

15. The method as claimed in claim 7 operable so that the sanitation device can move under motorized action upwardly and downwardly across the surface while directing and effecting the sanitation.

16. The method as claimed in claim 7 wherein the UV radiation source is arranged to run relatively vertically under motorized action in a track upwardly or downwardly and an arm is provided to direct the UV radiation source from the track so that the UV radiation source is enabled as to adopt different angles relative to the horizontal or vertical relationship.

17. A method as claimed in claim 7 and disposing a protective shield for a user with the ability to be in a surgery room to locate the UV radiation at the optimal location, height and angle relative to the surface thereby in use in a hospital environment being the surgery room containing a surgery bed and surgery equipment, the shielding and structure and action imparts the UV radiation without requiring room evacuation when cleansing is affected.

18. The method as claimed in claim 7 for sanitizing a floor surface; the device being selectively operable under motorized action upwardly and downwardly across the floor surface while effecting the sanitation, a wing movably directed downwardly under motorized action to clean the floor, and in the horizontal angle the wing being disposable horizontally, and optionally a sensor for establishing a degree of adjacency to the floor to provide for effective and efficient use.

19. The method as claimed in claim 7 wherein the sanitation source is operable under motorized action upwardly and downwardly across the surface while effecting the sanitation, moving a wing that mounts the sanitation source under motorized action such that the sanitation source is selectively directed downwardly horizontally to sanitize a floor, or directed vertically to sanitize flexible vertical surfaces with folds, and in the horizontal mode the device is selectively in close proximity horizontally and adjacent to the horizontal surface being sanitized, and in the vertical mode is in a close proximity arrangement to sanitize the flexible vertical surfaces with folds, and optionally a sensor for establishing the degree of adjacency to provide for effective and efficient use.

\* \* \* \* \*

UNITED STATES PATENT AND TRADEMARK OFFICE
CERTIFICATE OF CORRECTION

PATENT NO. : 11,413,361 B2
APPLICATION NO. : 16/782691
DATED : August 16, 2022
INVENTOR(S) : Kreitenberg et al.

It is certified that error appears in the above-identified patent and that said Letters Patent is hereby corrected as shown below:

In the Specification

In Column 2, Line 46, delete "position a" and insert -- position and --, therefor.

In Column 4, Line 7, delete "the" and insert -- of the --, therefor.

In Column 4, Line 18, delete "range" and insert -- range of --, therefor.

In Column 4, Line 47, delete "in to" and insert -- to --, therefor.

In Column 7, Line 2, delete "power" and insert -- of power --, therefor.

In Column 7, Line 10, delete "base side lamp (130)" and insert -- base side lamp (128) --, therefor.

In Column 10, Line 38, delete "angle the" and insert -- angle of the --, therefor.

In the Claims

In Column 11, Line 10, in Claim 1, delete "k)" and insert -- j) --, therefor.

In Column 11, Line 13, in Claim 1, delete "track," and insert -- track; --, therefor.

In Column 11, Line 15, in Claim 1, delete "l)" and insert -- k) --, therefor.

In Column 12, Line 14, in Claim 7, delete "k)" and insert -- j) --, therefor.

In Column 12, Line 17, in Claim 7, delete "track," and insert -- track; --, therefor.

In Column 12, Line 18, in Claim 7, delete "l)" and insert -- k) --, therefor.

Signed and Sealed this
Sixteenth Day of May, 2023

Katherine Kelly Vidal
*Director of the United States Patent and Trademark Office*

In Column 12, Line 22, in Claim 7, delete "m)" and insert -- l) --, therefor.

In Column 12, Line 25, in Claim 7, delete "the mobile" and insert -- of the mobile --, therefor.

In Column 12, Line 36, in Claim 8, delete "A method" and insert -- The method --, therefor.

In Column 13, Line 19, in Claim 17, delete "A method" and insert -- The method --, therefor.